United States Patent
Griffiths et al.

(10) Patent No.: US 10,416,168 B2
(45) Date of Patent: Sep. 17, 2019

(54) METHOD OF ANALYZING THE CONTENT OF DROPS AND ASSOCIATED APPARATUS

(71) Applicant: ECOLE SUPERIEURE DE PHYSIQUE ET DE CHIMIE INDUSTRIELLES DE LA VILLE DE PARIS, Paris (FR)

(72) Inventors: Andrew David Griffiths, Paris (FR); Raphaël Clément Li-Ming Doineau, Paris (FR); Clément Nizak, Paris (FR); Philippe Chi-Thanh Nghe, Saint-Mande (FR); Jean Marie Pierre Baudry, Paris (FR); Elodie Michéle Christine Brient-Litzler, Versailles (FR); Alexei Godina, Asnieres-sur-Seine (FR)

(73) Assignee: ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 139 days.

(21) Appl. No.: 15/519,490

(22) PCT Filed: Oct. 15, 2015

(86) PCT No.: PCT/EP2015/073942
§ 371 (c)(1),
(2) Date: Apr. 14, 2017

(87) PCT Pub. No.: WO2016/059182
PCT Pub. Date: Apr. 21, 2016

(65) Prior Publication Data
US 2017/0307626 A1 Oct. 26, 2017

(30) Foreign Application Priority Data
Oct. 15, 2014 (FR) .................................. 14 59903

(51) Int. Cl.
*G01N 33/543* (2006.01)
*G01N 33/68* (2006.01)
(Continued)

(52) U.S. Cl.
CPC ........ *G01N 33/68* (2013.01); *B01L 3/502715* (2013.01); *B01L 3/502761* (2013.01);
(Continued)

(58) Field of Classification Search
CPC ................ C12Q 1/6846; C12Q 1/6816; C12Q 2563/149; C12Q 2563/159;
(Continued)

(56) References Cited

U.S. PATENT DOCUMENTS 8,372,590 B2 2/2013 Bernard et al.
8,798,341 B2 8/2014 Baudry et al.
(Continued)

FOREIGN PATENT DOCUMENTS

EP 1750129 A2 2/2007

OTHER PUBLICATIONS

Preliminary Search Report for FR 1459903, completed Jul. 17, 2015.
(Continued)

*Primary Examiner* — Jennifer Wecker
(74) *Attorney, Agent, or Firm* — B. Aaron Schulman, Esq.; Stites & Harbison, PLLC

(57) ABSTRACT

The invention concerns a method of analyzing the content of drops, involving then following step:
providing a plurality of drops (6) contained in a carrier fluid, at least one of the drops (6) comprising at least one aggregate (10) of particles defining an object extending along a main axis, at least some of the drops (6) containing at least one target element capable of attaching to the aggregate (10).
(Continued)

The method involves a step in which a physical parameter characteristic of the attachment of the target element to the aggregate (10) is measured.

17 Claims, 21 Drawing Sheets

(51) Int. Cl.

| | | |
|---|---|---|
| *G01N 15/00* | (2006.01) | |
| *B01L 3/00* | (2006.01) | |
| *C12Q 1/6844* | (2018.01) | |
| *C12Q 1/68* | (2018.01) | |

(52) U.S. Cl.
CPC ...... *B01L 3/502784* (2013.01); *C12Q 1/6846* (2013.01); *G01N 33/543* (2013.01); *B01L 2200/0668* (2013.01); *B01L 2200/0673* (2013.01); *B01L 2300/0816* (2013.01); *B01L 2300/0864* (2013.01); *B01L 2400/0487* (2013.01); *G01N 2015/003* (2013.01); *G01N 2015/0092* (2013.01)

(58) Field of Classification Search
CPC ..... B01L 2200/0668; B01L 2200/0673; B01L 2300/0816; B01L 2300/0864; B01L 2400/0487; B01L 3/502715; B01L 3/502761; B01L 3/502784; G01N 2015/003; G01N 2015/0092; G01N 33/543; G01N 33/68
See application file for complete search history.

(56) References Cited

U.S. PATENT DOCUMENTS

| | | |
|---|---|---|
| 9,056,289 B2 | 6/2015 | Weitz et al. |
| 9,839,911 B2 | 12/2017 | Weitz et al. |
| 2008/0176289 A1* | 7/2008 | Zeng .................... G06T 7/11 435/91.2 |
| 2009/0246796 A1 | 10/2009 | Bernard et al. |
| 2010/0044586 A1* | 2/2010 | Duhr ................ B01L 3/502715 250/459.1 |
| 2010/0105112 A1 | 4/2010 | Holtze et al. |
| 2011/0275063 A1* | 11/2011 | Weitz ................ G01N 33/5008 435/6.1 |
| 2012/0015382 A1 | 1/2012 | Weitz et al. |
| 2012/0222748 A1 | 9/2012 | Weitz et al. |
| 2014/0342373 A1* | 11/2014 | Viovy ............... B01L 3/502784 422/504 |
| 2015/0314292 A1 | 11/2015 | Weitz et al. |
| 2015/0367346 A1* | 12/2015 | Foster ................ F16K 99/0046 435/288.7 |
| 2018/0056293 A1 | 3/2018 | Weitz et al. |

OTHER PUBLICATIONS

International Search Report for PCT/EP2015/073942, dated Feb. 1, 2016.
Written Opinion of the International Searching Authority for PCT/EP2015/073942, dated Feb. 1, 2016.
Tsuchiya et al: "On-chip polymerase chain reaction microdevice employing a magnetic droplet-manipulation system", Sensors and Actuators B: Chemical: International Journal Devoted to Research and Development of Physical and Chemical Transducers, Elsevier S.A., CH, vol. 130, No. 2, Oct. 18, 2007(Oct. 18, 2007), pp. 583-588, XP022550371, ISSN: 0925-4005 the whole document abstract p. 585, left-hand column, paragrah 1, p. 585, left-hand column, paragraph 2 page 585, right-hand column, paragraph 2, figures 3-5 p. 586, left-hand column, paragraph 1, p. 586, right-hand column, paragraph 2—p. 587, left-hand column, paragraph 1 p. 587, left-hand column, last paragraph.
Bruno Teste et al: "A low cost and high throughput magnetic bead-based immuno-agglutination assay in confined droplets", Lab on a Chip, vol. 13, No. 12, Mar. 26, 2013(Mar. 26, 2013), pp. 2344-2349, XP055202306, ISSN: 1473-0197, DOI: 10.1039/c3lc50353d the whole document abstract p. 2346, right-hand column, paragraph 1—p. 2347, left-hand column, paragraph 1; figs 1-2.
Mazutis, L., Gilbert, J., Ung, W. L., Weitz, D. A., Griffiths, A. D., & Heyman, J. A. (2013). Single-cell analysis and sorting using droplet-based microfluidics. Nature Protocols, 8(5), 870-891. http://doi.org/10.1038/nprot.2013.046.

\* cited by examiner

METHOD OF ANALYZING THE CONTENT OF DROPS AND ASSOCIATED APPARATUS

TECHNICAL FIELD

The present invention relates to a method for analyzing the content of drops comprising the following step:

providing a plurality of drops contained in a carrier fluid, at least one of the drops comprising at least an aggregate of particles defining an elongated object along a main axis, at least certain drops containing at least one target element able to be attached on the aggregate.

Such a method is intended for example for carrying out screening of molecules of interest dispersed in the drops. In particular, the method is intended for determining or even for selecting drops comprising a particular target element, this target element may result from a chemical reaction or a biological reaction.

In particular, the measurement and then the selection of the drops may be based on the concentration or connecting activity of a product.

BACKGROUND

Document WO 2009/011808 A1 describes a method for determining an activity for attaching a protein within a drop.

The publication "Single-cell analysis and sorting using droplet-based microfluidics", of Mazutis et al. published online, on Apr. 4, 2013 in the journal Nature Protocols illustrates this principle.

A mouse hybridoma is encapsulated in a drop with a bead covered with anti-mouse antibody. The hybridoma secretes antibodies. A secondary antibody coupled with a fluorophore gives the possibility of revealing the presence of the secreted antibody. The distribution of the secondary antibody is, in the absence of a secreted antibody, homogeneous in the drop, but is relocalized on the bead in the presence of antibodies.

The method is therefore very selective for determining the activity of a particular cell.

On the other hand, such a method has diverse drawbacks. The method for compartmentalizing the cells and the beads is random. The number of beads in the drops may be estimated by a Poisson distribution law. Also, the number of cells within the drops may be estimated by an independent Poisson distribution law. The initial concentrations of beads and drops are adjusted for having on average one cell and one bead per drop. Only a portion of the drops therefore is of interest for the achieved analysis.

Moreover, the presence of a single bead of a significant size per drop is not favorable to the resolution of the method. Indeed, the secondary antibodies are distributed over the whole surface of the bead. The dynamic range of the method is therefore limited by the external surface area available per bead.

SUMMARY

An object of the invention is to provide a more reliable and more sensitive analysis method than the existing methods.

For this purpose, the object of the invention is a method of the aforementioned type, characterized in that the method comprises a measurement step for measuring a physical parameter characteristic of the attachment of the target element on the aggregate.

The method according to the invention may comprise one or several of the following characteristics, taken individually or according to all the technically possible combinations:

the particles are magnetic particles, advantageously paramagnetic particles, preferably superparamagnetic particles;

the step for providing drops comprises:
  the dispersion of the particles in a mass of fluid intended to form the drops, and then
  the dispersion of the mass of fluid in the form of drops, the formation in each drop of at least one aggregate of particles defining an elongated object along a main axis, the particle aggregate being formed in each drop after the dispersion;

the target element is an element selected from the group formed by a protein, an antibody, a peptide, a DNA or RNA piece, a metabolite, an iron, a lipid and a biomolecule which may be produced by a cell;

at least certain drops comprise a productive entity which may produce the target element, the productive entity being preferably selected from the group formed by a cell or a system for expression in vitro;

the measurement step includes the measurement of the physical parameter locally in a plurality of points located in the drop, the measurement step preferably including the determination of the integral of the values measured within the drop;

the method comprises before the measurement step, a step for orienting the main axis of the aggregate along a detection axis;

the method comprises several measurement steps, with a step for orienting the main axis of the aggregate along a different detection axis for each of the measurements;

the measurement step is carried out in a microfluidic chamber without any circulation of the drops;

the method comprises:
the provision of a device comprising an assembly for putting in circulation the drop and a detection area;
the transport of the drop towards the detection area, the measurement within the drop being carried out in the detection area;

the method comprises:
the provision of a device comprising an assembly for putting in circulation the drop and a plurality of classification areas, and a means for directing the drop or a portion of the drop selectively towards a classification area,
the classification decision of the drop or of a portion of the drop, the decision consisting of selectively selecting a classification area from the plurality of classification areas,
the transport of the drop, respectively of a portion of the drop, towards the classification area of the drop selected during the decision step;

at least one drop comprises at least one target element, at least one first signaling entity able to form a complex with the target element and at least a second distinct signaling entity able to form a complex with the target element, the method comprising the measurement of a signal indicating the concentration of each of the signaling entities relocalized on the aggregate;

at least one drop comprises at least one target element, at least one signaling entity able to form a complex with the target element and at least a quantification entity able to form a complex with the target element, the method comprising:

the measurement of a signal representative of the concentration of the signaling entity relocalized on the aggregate, the measurement of a signal representative of the concentration of the quantification entity relocalized on the aggregate, the determination of the dissociation constant of the target element with the signaling entity from the ratio of the signal of the signaling entity relocalized on the signal of the quantification entity relocalized;

at least certain drops comprise a productive entity, the productive entity being a cell which may produce at least one antibody being a target element, the method comprising a step for determining the affinity of the antibody produced by the productive entity for at least one antigen, the method preferably comprising a step for sorting the drop after the determination step;

at least one drop comprises at least two distinct signaling entities, each of the two signaling entities being able to form a complex with a distinct target element on the aggregate, the method comprising the measurement of a signal indicating the concentration of each of the signaling relocalized entities;

at least certain drops comprise a productive entity, the productive entity being a cell which may produce one or several types of proteins, each protein being a distinct target element, the measurement of the signal indicating the concentration of each of the relocalized signaling entities allowing quantification of the type(s) of proteins;

the measurement of a physical parameter is a fluorescence measurement;

at least one of the drops comprises a cell capable of secreting the target element and the method comprises an incubation step during which the target element is secreted into the drop by the cell;

at least one of the drops comprises a cell and the method comprises a step for cell lyzis;

at least one of the drops comprises an in vitro translation system capable of expressing the target element;

the method comprises a step for measuring a physical parameter, locally in a first point located away from the aggregate in at least one of the drops and of the same physical parameter, locally in a second point in the vicinity of the aggregate in the same drop;

the maximum dimension of the particles is less than 50% of the diameter of the drop;

the drop contains at least one signaling entity, and the measurement of the physical parameter depends on the position of the signaling entity within the drop or relatively to the aggregate;

the productive entity produces several target elements selected from the group formed by a protein, a peptide, a DNA or RNA piece, a metabolite, an ion, a lipid and a biomolecular which may be produced by a cell;

the method includes a step for determining at least one characteristic of the productive entity;

the step for deciding classification takes place after the measurement step;

the drop contains superparamagnetic particles, the drop or the portion of the drop is directed towards the classification area by a directing means selected from among a magnetic force, an electric field, a dielectrophoresis, a electrocoalescence or a surface acoustic wave;

a portion of the drop is extracted by means of the magnetic force, the extracted portion forming an auxiliary drop and containing the aggregate.

The object of the invention is also an apparatus for analyzing the content of drops comprising:
    an assembly for providing a plurality of drops contained in a carrier fluid, at least one of the drops comprising at least one aggregate of particles defining an elongated object along a main axis, characterized in that the apparatus comprises an assembly for measuring a characteristic physical parameter of the attachment of the target element on the aggregate,
the apparatus further comprising, preferably:
    an assembly for circulating the drop,
    an assembly for deciding classification of the drop,
    an assembly for sorting the drop according to the classification decision.

BRIEF DESCRIPTION OF THE DRAWINGS

The invention will be better understood upon reading the description which follows, only given as an example, and made with reference to the appended drawings, wherein.

DETAILED DESCRIPTION

Figure 1:
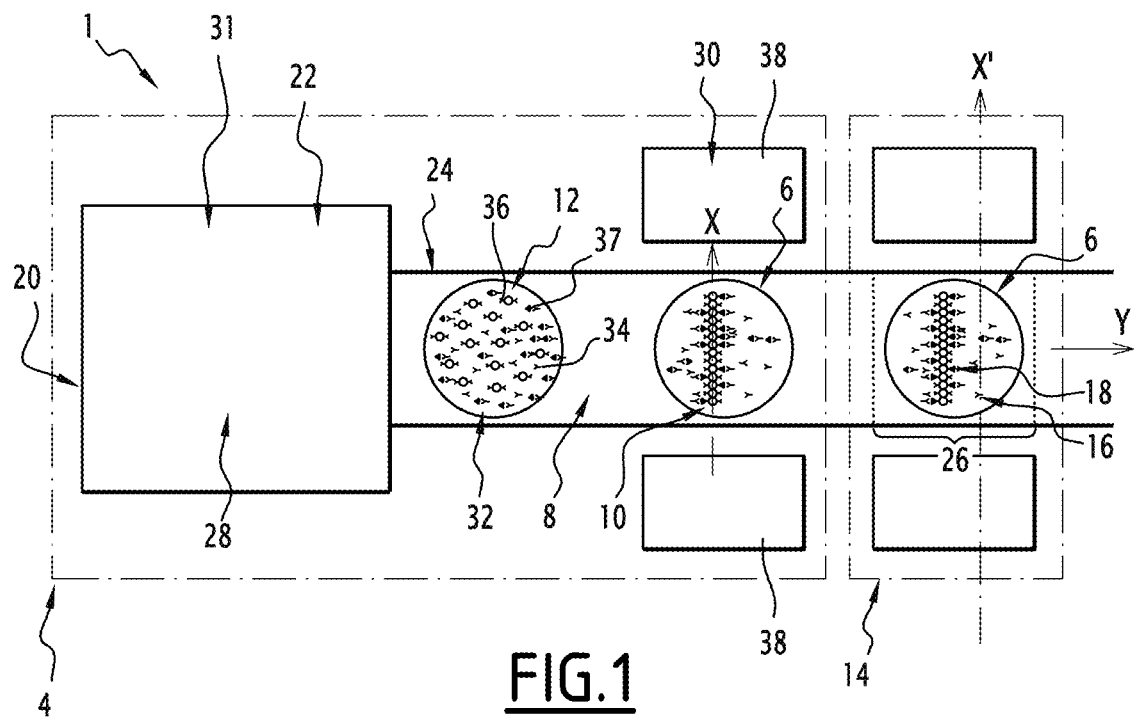
FIG. 1 is a schematic illustration of the target elements of a first analysis apparatus according to the invention.

A first apparatus 1 for analyzing the content of drops according to the invention is illustrated in FIG. 1.

The apparatus 1 comprises an assembly 4 for providing a plurality of drops 6 contained in a carrier fluid 8, at least one portion of the drop 6 comprising at least one aggregate 10 of particles 12 defining an elongated object according to a main axis X.

The apparatus 1 further comprises an assembly for measuring 14 a physical parameter in the drop.

The measurement assembly 14 is for example able to conduct the measurement of a physical parameter, locally in a first point 16 located away from the aggregate 10 in at least one of the drops and of the same physical parameter locally in a second point 18 in the vicinity of the aggregate 10 in the same drop.

The apparatus 1 also includes a device 20 comprising a circulating assembly 22, a circulation conduit 24 and a detection area 26.

The circulation assembly 22 is able to have each drop 6 circulate in the carrier fluid 8 in the conduit 24 as a train of successive drops.

The provision assembly 4 comprises a loading assembly 28 and an aggregation assembly 30. The provision assembly 4 further comprises a spacing apart assembly 31.

The loading assembly 28 is able to provide a plurality of initial drops 32 comprising a dispersion of particles 12, at least one of the initial drops 32 further comprising at least one target element 37.

Figure 13:
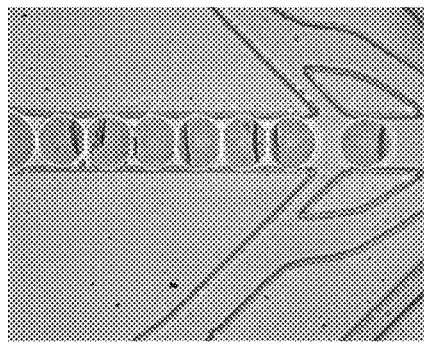
FIGS. 13 and 14 illustrate assemblies for spacing apart drops and for measurement.
Figure 14:
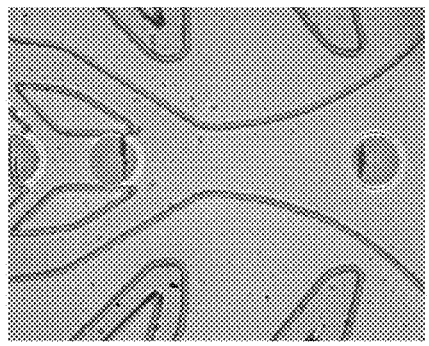

The spacing apart assembly 31 is able to space apart two successive drops 6 from the train of drops, i.e. of increasing the distance between two successive drops. For example, the spacing apart assembly 31 includes a carrier fluid inlet 8. Examples of spacing apart assemblies are illustrated in FIGS. 13 and 14.

The carrier fluid 8 is able to separate two successive drops 6 from the train of drops in order to prevent their contact. Alternatively, the separation of the drops 6 is carried out by a mechanical device.

The fluid forming the internal phase of the drops 6 and the carrier fluid 8 are substantially immiscible. For example, the drops 6 comprise an aqueous internal phase and the carrier fluid 8 is an organic or oily phase.

The carrier fluid 8 is advantageously a fluorinated oil.

The carrier fluid 8 or the fluid forming the internal phase of the drops advantageously comprises a surfactant able to prevent merging of two drops 6 in contact, such as for example as described in the US patent 2010/0105112 or further the surfactant EA from RainDance Technologies.

By "substantially immiscible", is generally meant that the solubility of the fluid forming the drops in the carrier fluid 8, measured at 25° C. and at ambient pressure, is less than 1%.

The size of the drops 6 is for example comprised between 1 μm and 1000 μm.

The volume of the drops 6 is advantageously comprised between 0.1 picoliters and 1 microliter.

The provided drops 6 are substantially monodispersed. This means that the polydispersity of the drops 6 is less than 5%.

In the illustrated example, the drops 6 are spherical. Alternatively, the drops 6 are of an elongated shape along the circulation axis Y of the conduit 24. Alternatively, the drops 6 are of the shape of a puck flattened along an axis perpendicular to the circulation axis Y.

Each initial drop 32 comprises a base fluid, a dispersion of solid particles 12 in the base fluid and a plurality of signaling entities 34. Further at least one initial drop 32 comprises at least one target element 37.

The particles 12 are intended to form the aggregate 10 of an elongated shape. For example, the particles 12 are superparamagnetic particles which acquire a magnetic moment upon applying a magnetic field. The superparamagnetism is a behavior of ferromagnetic or ferrimagnetic materials which appears when they are in the form of small grains or nanoparticles. In grains of a sufficiently small size, the magnetization may spontaneously reverse under the influence of temperature. The term of "magnetic particles" in the text designates superparamagnetic particles.

The magnetic particles 12 are for example selected from among the particles provided by Dynal (Life Technologies) or Ademtech or Miltenyi.

The particles 12 are for example nanometric. Thus, their maximum dimension is less than 1 μm and is for example comprised between 50 nm and 1,000 nm. The particles 12 are advantageously substantially monodispersed. For example, the variation between the maximum dimensions of the particles 12 is strictly less than 10%. The size and the number of particles 12 per drops 6 are selected so as to form the desired number of aggregates. The maximum dimension size of the particles 12 is less than 50% of the diameter of the drop 6.

The concentration of particles 12 allows colloidal stability.

The concentration of particles 12 per drop 6 is such that the particles 12 occupy between 0.1% and 5% of the volume of the drop 6, for example 1.7%.

In an example, each drop 6 of 33 picoliters on average contains 500 particles 12 with the diameters of 300 nm.

The particles 12 initially form a homogeneous dispersion in the initial drops 32. They are substantially uniformly distributed in the volume of the initial drop 32. Thus, the concentration of particles 12 is homogeneous on the whole of the initial drop 32.

The particles 12 advantageously have a surface allowing coupling of biological molecules, consisting of a surface material. For example, the particles 12 are covered with a polymer having COOH or $NH_2$ functions.

Advantageously, this surface material also gives the possibility of limiting spontaneous aggregation of the particles 12 in the drop.

Additionally, it may advantageously promote the stability of the aggregate 10, for example via non-specific bonds between the material of a bead and of its neighbor in the aggregate.

The particles 12 are advantageously functionalized. This notably means that the surface material of the particles 12 includes functional elements.

In the illustrated example, the functional elements include a capture element 36. The capture element 36 is for example able to capture the target element 37. The capture element 36 is able to indirectly bind to the signaling entity 34 via the target element 37. Alternatively, the capture element is able to be directly bound to the signaling entity 34.

For example, the capture element 36 on the particles 12 is a protein G, the target element 37 is an antibody, capable of binding to the protein G and the signal entity 34 is an antigen recognized by the antibody, the antigen being able to bind to the antibody.

The aggregation assembly 30 is able to generate an aggregation of the particles 12 along a main axis X.

The aggregation assembly 30 for example includes two magnets 38 located on either side of the conduit 24. The magnetic field is not parallel to the circulation axis Y and advantageously perpendicular to the circulation axis Y. The aggregation assembly 30 allows the formation of an elongated aggregate in each drop 6.

In an embodiment, the magnets 38 are permanent magnets.

Alternatively, the aggregation assembly 30 includes a non-permanent magnet.

Alternatively, the aggregation assembly 30 is able to switch from an active mode to an inactive mode in order to generate elongated aggregates 10 only in certain drops.

Each aggregate 10 of particles 12 for example includes a column oriented along a main axis X. The height of the column is advantageously comprised between 50% and 100% of the diameter of the drop 6. Its width is for example less than 60% of its height.

Further, the aggregation assembly 30 is for example able to orient the aggregate along a preferential axis. In the illustrated example, the axis X of the aggregate 12 is perpendicular to the circulation axis Y of the drop 6 in the circulation conduit 24.

The measurement assembly 14 for example comprises a laser line able to measure optically the intensity of the fluorescence along a line extending along an axis X' perpendicular or tilted relatively to the circulation axis Y.

The measurement assembly 14 is able to conduct the measurement within the drop in the detection area 26.

The axis X' of the laser line is advantageously parallel to the axis of the aggregate X in the detection area 26.

When the flow rate of the carrier fluid 8 is constant, the measurement overtime of the signal obtained by the laser line corresponds to spatial scanning of the drop 6 passing in front of the laser line. This gives the possibility of successively assuming several measurement points and in particular at least one first measurement point 16 located away from the aggregate 10 and a second measurement point 18 located closer to the aggregate 10 in the vicinity of the aggregate 10.

In practice, a plurality of successive measurement points are taken on over the longitudinal dimension of the drop 6 during its gradual passing facing the measurement assembly 14.

Figure 2:
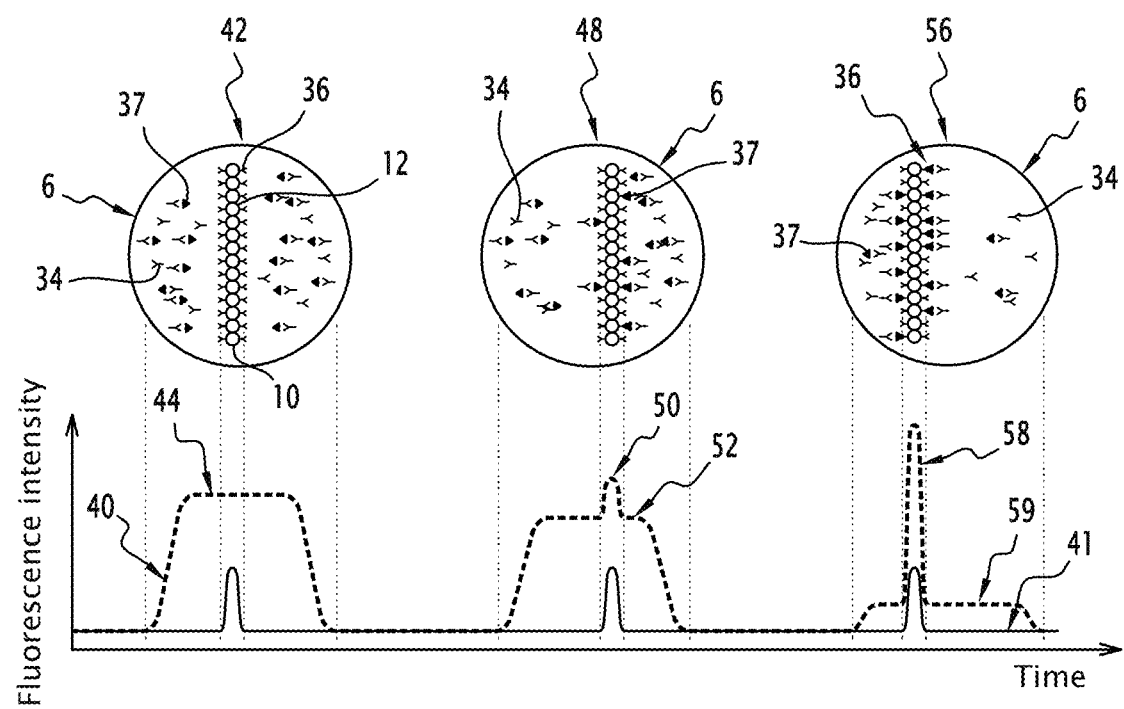
FIG. 2 is a schematic illustration of a method step with the first apparatus.

In the example illustrated in FIGS. 1 and 2, the signaling entity 34 is fluorescent. The circulation conduit 24 is intended to allow circulation of the drops 6, 32 along the circulation axis Y in the circulation direction from the provision assembly 4 to the measurement assembly 14.

The circulation conduit 24 advantageously has an inner diameter of less than or equal to 1 mm.

The circulation conduit 24 is elongated along the circulation axis Y. The circulation conduit 24 has an inter cross-section with a rounded contour such as circular or elliptical, or with a polygonal conduit such as a rectangular contour.

The circulation conduit 24 is for example defined in a translucent material allowing the measurement of optical parameters by the measurement assembly 14. Alternatively, the circulation conduit 24 defines at least one transparent measurement window in the detection area 26.

The walls of the circulation conduit 24 are impervious to the carrier fluid 8.

For example, the circulation conduit 24 is defined in a capillary tube with an inner dimension advantageously less than 1 mm. Alternatively, the circulation conduit 24 is defined in a microfluidic chip.

The assembly for circulating the drops 22 is intended to move one by one the drops 6, 32 in the conduit 24 in the circulation direction.

The circulation assembly 22 for example comprises a syringe pump giving the possibility of applying controlled flow rates to the carrier fluid 8. Alternatively, the circulation assembly 22 comprises a pressure controller.

A first analysis method according to the invention applied in the first apparatus 1 will now be described.

An apparatus 1 as described earlier is provided. Initial drops 32 like those described above are prepared in a carrier fluid 8.

Preferably, the particles 12 are dispersed homogenously in each initial drop 32. Taking into account the small size of the individual particles 12 relatively to the initial drops 32, each initial drop 32 contains a large number of individual particles 12 for example greater than 10. The probability of obtaining an initial drop 32 without any particles 12 is very low, or even zero.

Preferably, the target elements 37 and the signaling entities 34 are dispersed homogeneously in each initial drop 32.

Within the initial drop 32, bonds are formed between the elements having particular affinities.

In one example, each target element 37 is bound to a signaling entity 34 and to a capture element 36. The signaling entity 34 is thus re-localized on a particle 12.

In the following, by "re-localized" entities are meant entities bound to the aggregate 10.

The initial drops 32 are put into circulation together with the carrier fluid 8 in the conduit 24 by the circulation assembly 22.

At least one initial drop 32 is conducted towards the aggregation assembly 30. An aggregate 10 of particles 12 defining an elongated object along a main axis X is formed by the aggregation assembly 30 in the initial drop 32.

Preferably, when the particles 12 are magnetic particles, they align along the main axis X during their passage in front of each magnet 38 of the aggregation assembly 30.

The drop 6 comprising the elongated object is conveyed towards the detection area 26. A physical parameter is measured locally by the measurement assembly 14 in at least one first point 16 in at least one of the drops 6.

In a particular application, a physical parameter is measured locally by the measurement assembly 14 in at least one first point 16 in at least one of the drops 6 and the same physical parameter is locally measured in at least one second point 18 in the vicinity of the aggregate 10 in the same drop 6 by the measurement assembly 14.

FIG. 2 illustrates as an illustration different measurements obtained for different drops 6. The graph illustrates the fluorescence intensity measured by the laser line overtime.

The fluorescence intensity is measured in a range of wavelength characteristic of the signaling entity 34. In the example, the fluorescence intensity is further measured in a range of wavelength characteristic of the particles 12, the particles 12 being fluorescent. The aggregate 10 is thus more easily locatable.

The fluorescence intensity 40 corresponding to the fluorescence of the signaling entity 34 measured on the laser line is shown in dotted lines in FIG. 2 for different drops 6.

The fluorescence intensity 41 corresponding to the fluorescence of the particles 12 is shown in solid lines in FIG. 2 for different drops 6.

The measurement step includes the determination of the physical parameter locally in a plurality of points located in the drop. It further advantageously comprises an accumulation of the measured values in a plurality of points, for example the determination of the integral of the measured values within the drop 6.

The first illustrated drop 42 is a drop 6 in which the different signaling entities 34 have not been re-localized on the particles 12. The distribution of the signaling entities 34 is homogeneous within the drop 6. A fluorescence intensity signal is measured as a plateau 44.

The second illustrated drop 48 is a drop 6 in which a portion of the signaling entities 34 has been re-localized on the particles 12. Indeed, these signaling entities 34 are bound to a target element 37 captured by the capture element 36. The fluorescence intensity in the vicinity of the aggregate 10 is then more significant than in the remainder of the drop 6. A fluorescence intensity signal having a peak 50 in addition to a plateau 52 is measured.

The height of the plateau 52 of the second drop 48 is smaller than the height of the plateau 44 of the first drop 42 since less signaling entities 34 are free away from the aggregate 10.

The third illustrated drop 56 is a drop in which a more significant proportion of the signaling entities 34 has been re-localized on the aggregate. A fluorescence intensity signal has a peak 58 and a plateau 59. The measured height of the peak 58 is larger than the height of the peak 50 measured in the second drop 48 since more signaling entities 34 are captured by the particles 12 and are therefore located in the vicinity of the aggregate 10.

Figure 9:
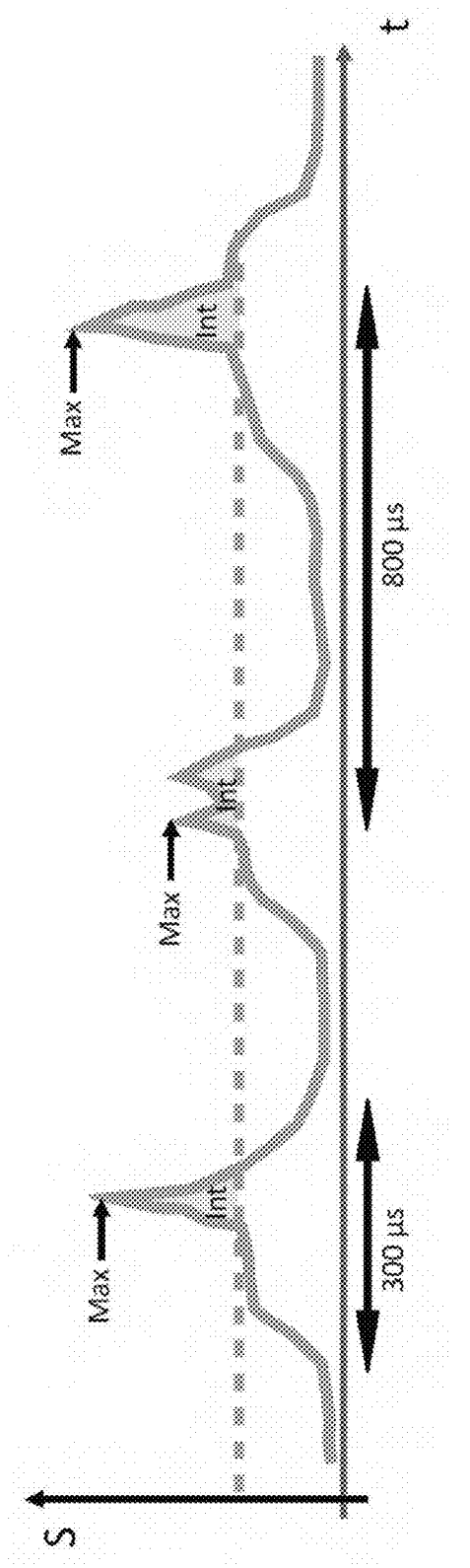
FIG. 9 is a schematic illustration of a method step with the first apparatus.

FIG. 9 illustrates the selection of the useful parameters for estimating the concentration of re-localized signaling entities 34.

In FIG. 9, which illustrates the signal S over time t, three drops are seen containing one (on the left and on the right) or two (aggregates) which have a higher signal peak. The useful parameter may be the maximum of the signal (indicated as Max) where the integral of the signal with respect to a given threshold (Int).

A first method consists of estimating this concentration by the maximum value of the signal (Max) in each drop 6, i.e. the height of the signal peaks re-localized on the aggregate.

A second method, more accurate, consists of calculating the integral of the signals (Int) for each drop 6 beyond a threshold set by the user, as for example illustrated in FIG. 9. This method may prove to be more interesting for limiting the dispersion of the signal, as this will be illustrated in example 3.

Both of these signal processing methods may be carried out in real time.

Other methods, for example combining these approaches may be applied, for example for measuring both the re-localized and non-re-localized signaling entities 34.

The invention further allows measurement of the concentration of the target element 37 in the drop 6.

A simple case for doing this is to put oneself in the case when:
- the capture element 36 is in a sufficient amount and with sufficient affinity for the target element 37 in order to capture at least more than 90% of the target element on the aggregate, advantageously the totality;
- the concentration of the signaling entity 34 is greater than that of the target element 37 and the dissociation constant Kd between the signaling entity 34 and the target element 37 is less than the concentration of the target element 37, advantageously by a factor of more than 10. This is typically the case when optimized dosage reagents are used like monoclonal antibodies with a subnanomolar Kd, and when the intention is to detect concentrations of the target element 37 greater than 1 nanomolar, as illustrated in Example 5.

By "nanomolar" is meant equal to 1 nanomole/L.

Under these particular conditions, the presence of each target element 37 gives rise to the formation of a capture element 36—target element 37—signaling entity 34 complex. The concentration of the target element 37 is therefore proportional to the signal of the signaling entity 34 re-localized on the aggregate 10. Other conditions give the possibility of achieving the quantification and will be obvious to one skilled in the art by modifying the concentrations and the affinities of the capture elements 36, or of the signaling entities 34 for the target element 37.

The FIGS. 3 to 6 illustrate a portion of a second apparatus 60 according to the invention.

This second apparatus 60 differs from the first apparatus 1 in that the device 20 includes a chamber 62. The chamber 62 includes a plurality of circulation passages 64 and a plurality of separation pads 66.

Other chambers are possible. In an alternative, chambers do not comprise separation pads as described in the document PCT/FR2009/051396 and illustrated in FIGS. 15 and 16.

The chamber 62 is intended to store a plurality of drops 6 in a carrier fluid 8 during an aggregation step or an orientation step and during the measurement step.

The measurement assembly of the second apparatus 60 differs from the measurement assembly 14 of the first apparatus 1 in that it is able to measure the physical parameter simultaneously on several drops 6 present in the chamber 62.

Figure 3:
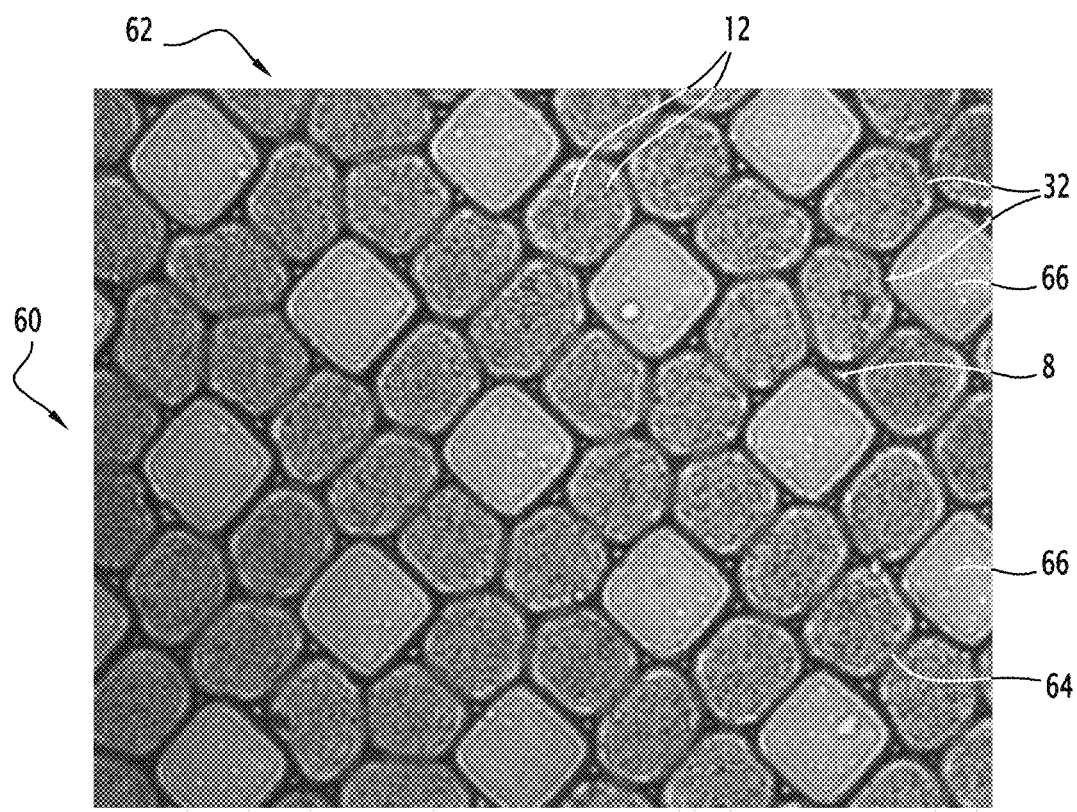
FIGS. 3 to 6 are photographs of a portion of a second apparatus according to the invention during the different method steps according to the invention.

FIG. 3 shows the chamber 62 containing initial drops 32 in a carrier fluid 8. The dispersion of the magnetic particles 12 is visible.

Figure 4:
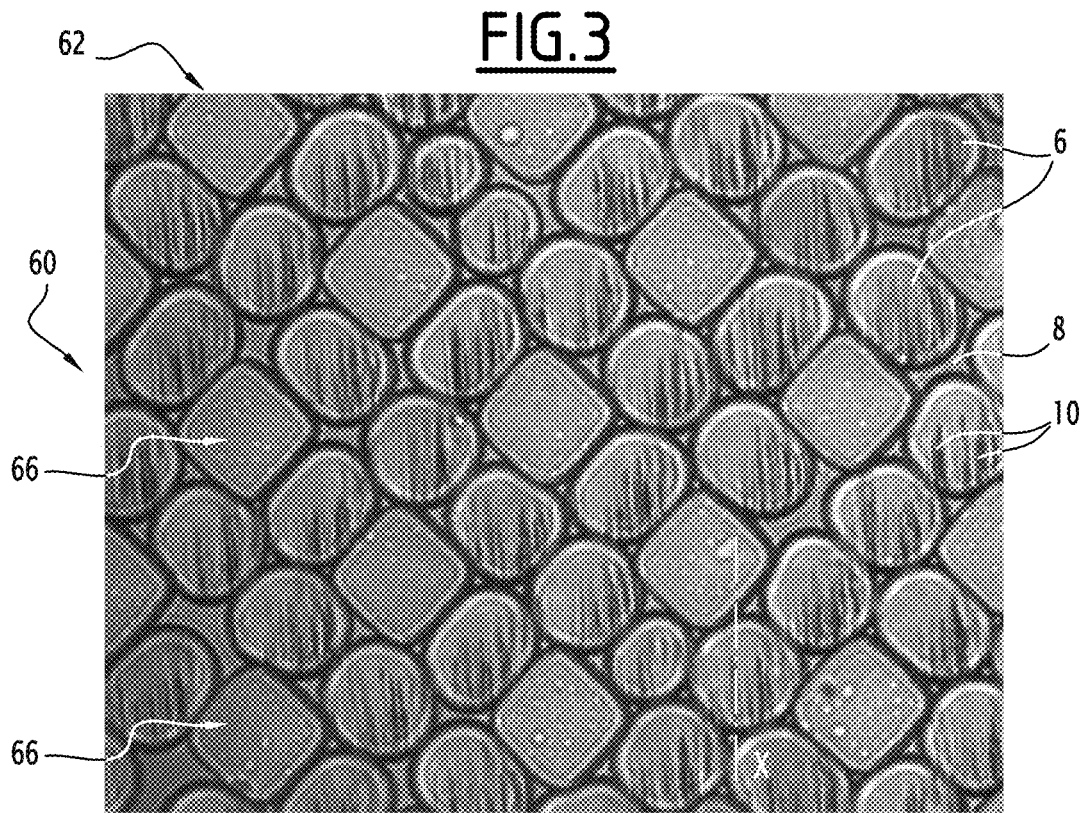

FIG. 4 shows the same chamber 62 after formation of the aggregates 10 in the drops. A plurality of elongated aggregates is formed in each drop 6.

Figure 5:
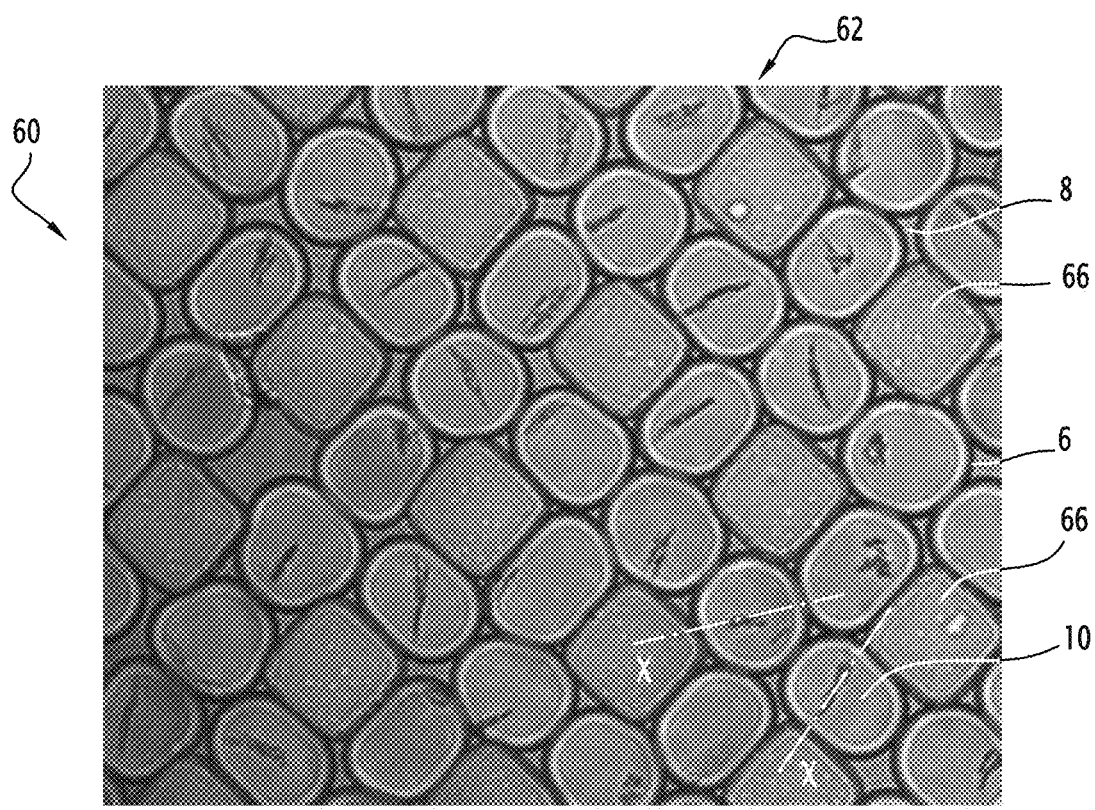

FIG. 5 shows in a same device 60 a plurality of drops 6 having elongated aggregates 10. The nature and the amount of drops 6 have been adjusted so that only a single elongated aggregate 10 is present per drop. The presence of a single aggregate 10 per drop 6 facilitates measurement.

Figure 6:
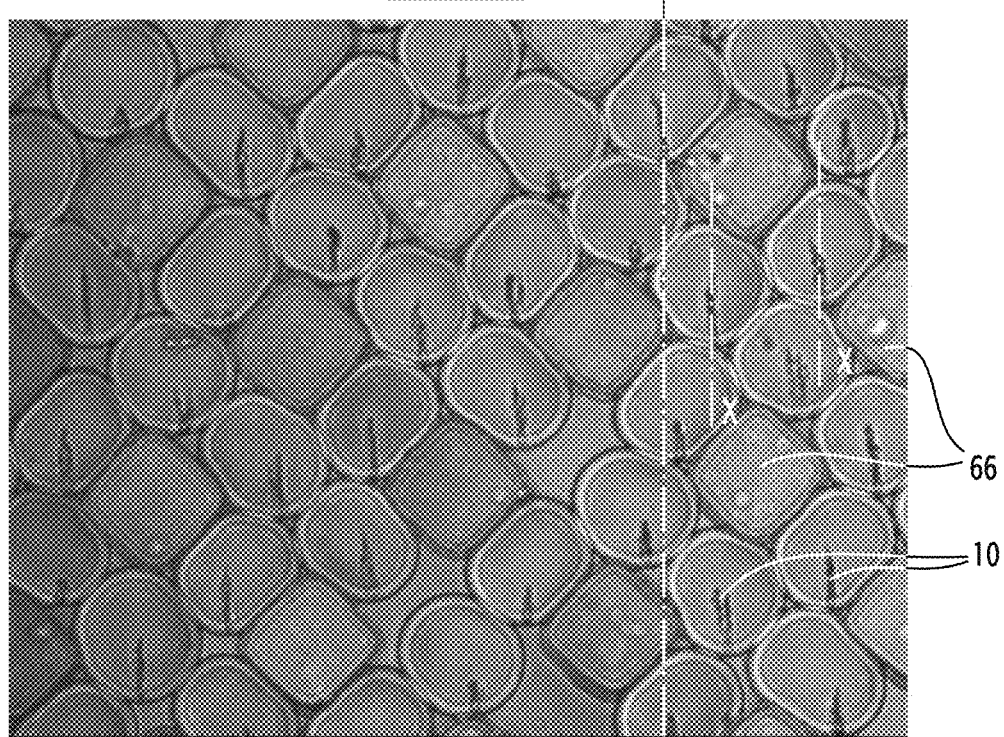

FIG. 6 shows the same chamber 62 after a step for orientation of the aggregates along a same detection axis D.

The analysis method according to the invention from this second apparatus 60 differs from the method described earlier in that the measurement is carried out on the plurality of drops 6 simultaneously, for example by measurement in the whole chamber 62 at the same time and not by circulation of the drop 6 in front of a detector.

The method also differs in that it comprises before the measurement step, a step for orientation of the main axis X of the aggregate 10 along a detection axis D.

Advantageously, the detection axis may be multiplied, by applying magnetic fields of variable orientation. This approach has the advantage of allowing discrimination of the aggregate 10 of other non-magnetic objects of the drop, or reduction of the parasitic signals. For example, the background fluorescence noise may be reduced. For example, the detection along different axes gives the possibility of distinguishing a re-localization of the signaling entity 34 on an aggregate 10 of a re-localization of the signaling entity 34 on another object of the drop 6, for example on a cell.

An implementation of this idea consists of applying a magnetic field B1 for aligning the main axis X of the aggregate 10 along a first orientation D1, and then of applying a magnetic field B2 perpendicular to B1 for aligning the main axis X of the aggregate 10 along a second orientation D2 perpendicular to D1.

Figure 7:
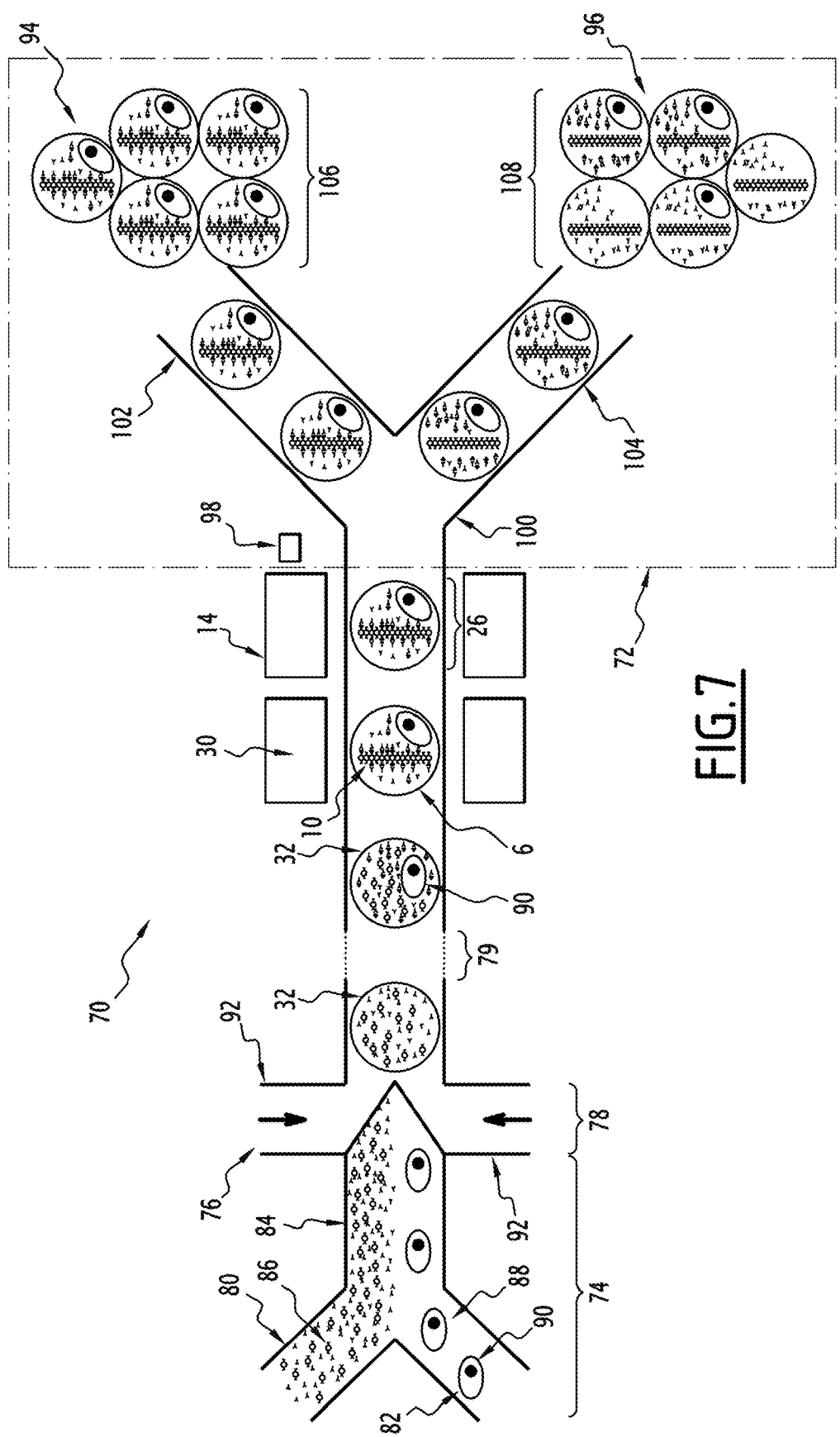
FIG. 7 is a schematic illustration of a third apparatus according to the invention.

A third apparatus 70 according to the invention is illustrated in FIG. 7.

This third apparatus 70 differs from the first apparatus 1 in that it further comprises a classification assembly 72.

Further, the third apparatus 70 differs from the first apparatus 1 in that the loading assembly 28 comprises an area 74 for entry of the internal phase and an area for entry of the carrier fluid 76 and a junction area 78. The loading assembly 28 further comprises an incubation area 79.

The area for entry of the internal phase 74 includes a first inlet conduit 80, a second inlet conduit 82 and a joint flow conduit 84.

The first inlet conduit 80 is intended for introducing the first mass of fluid 86 intended to form a portion of the internal phase of the drops. In the example, the first mass of internal fluid includes the particles 12 and a plurality of signaling entities 34.

The second inlet conduit 82 is intended for entry of the second mass of fluid 88 intended to form a portion of the internal phase of the drops. In the example, the second mass of internal fluid includes a suspension of productive entities 90 of the target element 37. The productive entities 90 are for example cells 90.

The cells 90 are advantageously cells able to secrete a target element 37. In particular, certain cells 90 are cells secreting antibodies likely hybridomas or plasmocytes. The secreted antibodies are recognized both by the capture elements 36 of the particles 12 and by the signaling entities 34.

The presence of these target elements 37 in the drop 6 allows re-localization of the signaling entities 34 on the aggregate 10.

The concentration of the cells 90 in the second mass of fluid is advantageously such that a significant proportion of drops contain only one cell 90, for example more than 10% of the drops contains a cell 90.

The joint-flow conduit 84 allows a distribution of both masses of fluid 86, 88 intended to form the internal phase.

The inlet area of the carrier fluid 76 is intended for entry of the carrier fluid 8. in the illustrated example, the carrier fluid 8 enters through to two inlet conduits 92.

The junction area 78 joins the inlet area of the carrier fluid 76 and the inlet area of the internal phase 74. In particular, the junction area joins the joint-flow conduit 84 up with the inlet conduits 92 of the carrier fluid.

Figure 11:
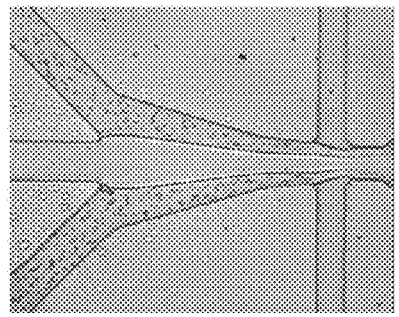
FIGS. 11 and 12 illustrate devices for generating drops.
Figure 12:
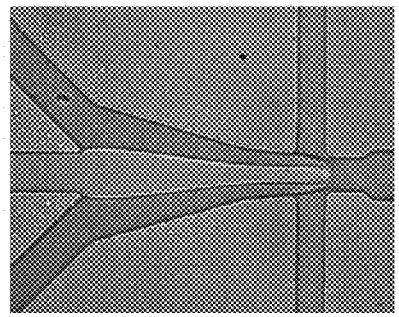

The junction area 78 is able to form initial drops 32. The junction area 78 illustrated here is a hydrodynamic focusing junction. Examples of hydrodynamic focusing junctions are illustrated in FIGS. 11 and 12. Alternatively, the initial drops 32 are formed in a junction T.

The initial drops 32 comprising a mixture of both masses of fluids 86, 88 are formed. The initial drops 32 comprise a dispersion of particles 12 and of signaling entities 34.

At least certain initial drops 32 further comprise a cell 90.

The incubation area 79 is located downstream from the junction area 78. The incubation area is intended for allowing secretion of the target element 37 by the cells 90. Alternatively, the cells 90 are intended to be lyzed in the incubation area 79 so that the target element 37 is released.

Alternatively, the incubation is carried out outside the device 20.

The third apparatus 70 also differs in that the device 20 further comprises a plurality of classification areas 94, 96 and a means 98 for directing the drop or a portion of the drop selectively towards a classification area 94, 96.

The classification areas 94, 96 are located downstream from the detection area 26. The conduit 24 includes a fork 100 in two outlet conduits 102, 104. The first classification area 94 includes the first outlet conduit 102 intended to receive a first group of drops 106. The second classification area 96 includes the second outlet conduit 104 intended to receive a second group of drops 108. Alternatively, the device 20 includes a larger number of classification areas 94, 96 according to the number of sort criteria.

The means 98 for directing the drops selectively is for example capable of directing one drop 6 towards a classification area 94, 96 by means of a magnetic force.

Alternatively, the drops 6 are directed by means of electrodes.

For example, the drops are directed towards a classification area, by dielectrophoresis, by electrocoalescence with a stream or by surface acoustic waves (SAW).

The analysis method with the third apparatus 70 according to the invention will now be described.

An apparatus 70 as described earlier is provided. A suspension of magnetic particles 12 and of signaling entities 34 is prepared and injected into the first inlet conduit 80.

A suspension of cells 90 is prepared and injected into the second inlet conduit 82.

A carrier fluid 8 is provided and injected into the conduits for entry of a carrier fluid 92.

The fluids 86, 88 are set into motion by means of circulation assemblies 22. The initial drops 32 are formed in the junction area 78.

The method further includes an incubation step during which the compartmentalized cell 90 secretes the target element 37, for example the protein to be analyzed.

Alternatively, the method includes a step for cell lyzis allowing the release of the target element 37, for example, the protein to be analyzed outside the cytoplasm.

These lyzes or incubation steps are carried out in the incubation area 79 of the device 20.

Alternatively, these steps are carried out outside the device 20.

The steps for forming the aggregate 10 and the measurement steps are the same as for the analysis method with the first apparatus 1.

The method differs in that the measurement step is followed by an analysis step. The analysis step gives the possibility of determining to which group 106, 108 belongs a drop 6 according to predetermined criteria and of generating a classification decision per drop 6 after the measurement step.

According to the classification decision, the drop 6 is directed towards one of the classification areas 94, 96 by the directing means 98.

In the example illustrated in FIG. 7, the drops 106 in which the strong fluorescence intensity signal is localized in majority in the vicinity of the aggregate 10 are directed into the first classification area 94. The drops of the first group 106 for example correspond to the third drops 56 of FIG. 2.

These drops 106 contain for example cells 90 able to generate a protein of interest. The drops 106 are optionally recovered so that their content is analyzed by other techniques or so that the cells 90 are again put into cultivation.

The drops 108 in which a different signal, notably a substantially homogeneous signal on the drop 108, was measured, are directed towards another classification area 96. The second group of drops 108 for example includes drops not comprising any cells 90 and drops containing cells 90 not producing the protein in a sufficient amount and quality.

Figure 8:
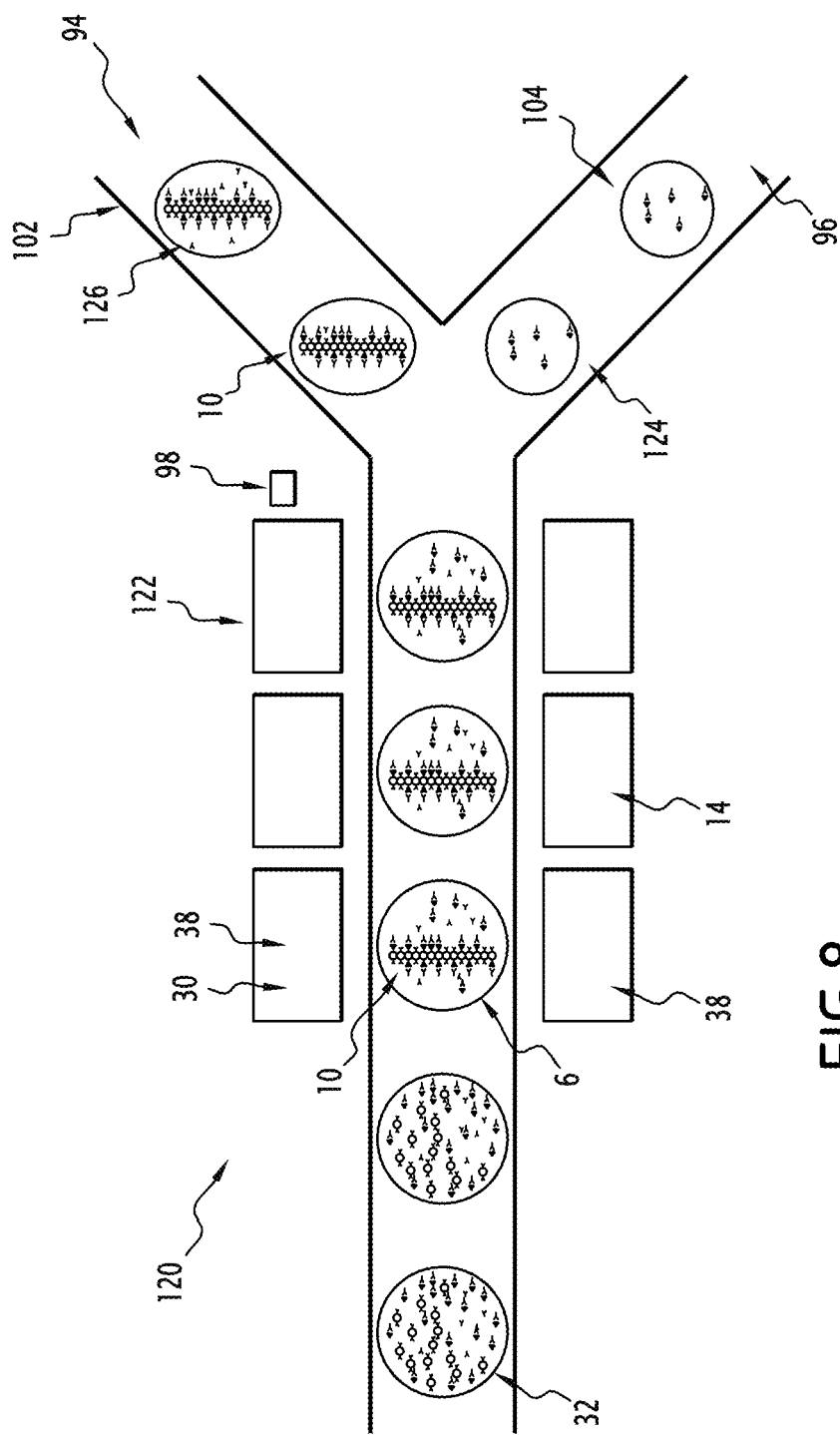
FIG. 8 is a schematic illustration of a fourth apparatus according to the invention.

A fourth apparatus 120 according to the invention is illustrated in FIG. 8. This apparatus 120 differs from the first apparatus 1 in that it further comprises an extraction assembly 122.

The extraction assembly 122 is able to separate the drop 6 into two extracted drops 124, 126, a primary drop 124 and an auxiliary drop 126, the auxiliary drop 126 comprising the aggregate 10.

Advantageously, the particles 12 are magnetic and the extraction assembly 122 is able to apply a magnetic force for achieving the extraction.

Further, the fourth apparatus 120 comprises downstream from the extraction assembly 122, a classification assembly 72 similar to that of the third apparatus 70 according to the invention giving the possibility of separating the auxiliary drops 126 from the primary drops 124.

In an alternative, the classification and extraction assemblies are the same.

Such an apparatus 120 is notably useful for achieving the selective capture by means of the elongated aggregates 10. The target elements 37 captured by the particles 12 are intended to be eluted after recovery of the selected drops.

A fifth apparatus according to the invention differs from the first apparatus in that it includes an additional injection device and a second detection area. The additional injection device is able to add elements into the drop after the detection.

The additional injection device is for example a device for merging the drop or a device for pico-injection.

The analysis method according to the invention from this fifth apparatus includes an injection step after the measurement step, and a measurement step after the injection step.

For example, the signaling entity 34 is fluorescent and a non-fluorescent additional entity is added during the additional injection step. The additional entity has the same characteristics as the signaling entity 34 except for its fluorescence. For example, the additional entity has the same affinity for the target element 37 than the signaling entity 34. During the first measurement step, the capture level of the fluorescent signaling entities 34 is determined. After the injection, the additional entities and the signaling entities 34 are competing for binding to the target element 37 in the vicinity of the aggregate 10.

The second measurement is carried out after a certain time and gives the possibility of determining the release rate of the fluorescent signaling entities 34 and therefore determining the dissociation constant $K_{off}$ of the bond between the signaling entity 34 and the target element 37.

The use of a dispersion of particles 12 of small sizes relatively to the size of the drops ensures a homogeneous distribution of the particles 12 in the drop 6, and therefore the quasi sure formation of an aggregate 10 of a significant size in each drop 6.

Globally, this method gives the possibility of dosing, quantifying an analyte in the drop. The formation of an elongated aggregate 10 gives the possibility of obtaining a better signal-to-noise ratio and a larger dynamic interval as compared with the test described in Mazutis et al. (Nat prot 2013) wherein a single bead is encapsulated. Indeed, the signal generated by the signaling entity 34 will be concentrated on a smaller width than that of a sphere of equal surface area. The height of the peak as shown in FIG. 2 will therefore be higher than in the case of a single bead for a same number of re-localized signaling entities 34.

This method may be used in many biological analysis methods.

The method according to the invention may apply to many types of analytes, biomolecules, polypeptides, proteins, metabolites, nucleic acids, cells, organelles, microparticles and nanoparticles, polymers, colloids, infectious agents, food compounds, environmental samples.

The apparatus according to the invention may be integrated as a technological brick in more complex devices in particular in a high flow rate screening device, in an on-chip laboratory, in a "point of care" device in laboratory instruments, robots or other devices.

Further, the method according to the invention may be integrated into complex procedures giving the possibility of diagnostic, discovery of drugs, discovery of targets, evaluation of a drug.

Further, the microfluidic systems according to the invention and the methods according to the invention may be combined or included in other types of microfluidic components or for other microfluidic functions known in the state-of-the-art.

Further, because of the small size of the samples used, the invention is particularly of interest for applications in the cell tests, in particular for screening single cells and in the digital biology.

By digital, is meant that the biological operations are carried out on a single copy of the chemical or biological object and that the result of the operation of each of the single copies may be isolated, as opposed to operations carried out on a set of such biological objects.

By biological or chemical objects, is meant any molecular, supra molecular crystalline, colloidal, cell, subcell, including in a non-exhaustive way, cells, organelles, viruses, modified natural DNA or artificial DNA, RNA or other nucleic acids, proteins, glycoproteins, forceful proteins, artificial or natural proteins, lipids, phospholipids, organic molecules, organometallic molecules, macromolecules, isolated crystals, quantum dots or quantum points, nanoparticles, vesicles, microcapsules and other entities.

The invention may further be particularly useful in a combination with diverse optical methods, notably optical detection methods.

The method may be applied for example for determining the presence of a target element 37 in a solution, the concentration of a target element 37 in a solution which allows establishment of affinity characteristics of a target element 37 with another species present on the particles 12 or in the drop 6.

The invention also allows measurement of the dissociation constant Kd between the target element 37 and a signalling entity 34.

In this case, the drop 6 further comprises quantification entities which have different fluorescence from the signalling entity 34.

More specifically, the definition of the dissociation constant Kd of the pair A:B between the element A (target element 37) and the element B (signalling entity 34) is:

$$Kd=[A_{free}][B_{free}]/[A:B]$$

wherein:

$[A_{free}]$ is the concentration of A not bound to B in solution, $[B_{free}]$ is the concentration of B not bound to A in solution,

[A:B] is the concentration of the complex A; B in solution, wherein A is bound to B.

The total concentration of the species A is:

$$[A_{total}]=[A_{free}]+[A:B]$$

the total concentration of species B is:

$$[B_{total}]=[B_{free}]+[A:B]$$

The concentration $[B_{total}]$ of the signalling entity 34 in the drop 6 is selected by the user and known.

The concentration $[A_{total}]$ may not be known a priori, for example when A is a target element 37 secreted by a cell 90 encapsulated in the drop 6.

The invention gives the possibility of measuring the concentration of the complex [A:B] re-localized on the aggregate VR the signalling entity signal 34.

This measurement may give access to an estimation of the dissociation constant Kd between A and B under controlled concentration conditions, where the quantification of A is achieved via a quantification entity which is another signalling entity 34.

A simple case for doing this is to place oneself in the case when:
- the capture elements 36 is in a sufficient amount and of a sufficient affinity for the target element 37 for capturing more than 90% of the target element 37, A on the aggregate 10, advantageously the totality,
- the concentration of the signalling entity 34 is greater than that of the target element 37,
- the concentration of the quantification entity used for quantifying A is greater than that of the target element 37 and the dissociation constant between the quantification entity and the target element 37 is less than the concentration of the target element 37, advantageously by a factor greater than 10.

The particular conditions, the presence of each target element 37 gives rise to the formation of a capture element 36—target element 37—quantification entity complex or/and the to the formation of a complex formed with the capture element 36—the target element 37—the signalling entity 34.

The number of the capture element 36—the target element 37—the signalling entity 34 complex is directly related to the Kd of the target element 37 for the signalling entity 34 through the following equation:

$$K_d = A * \frac{B}{[A:B]} = (A_{total} - [A:B]) * (B_{total} - [A:B])/[A:B]$$

i.e. $[A:B] =$ $$\left(A_{total} + B_{total} + K_d - \sqrt{(A_{total} + B_{total} + K_d) - 4 * A_{total} B_{total}}\right)/2$$

There exist conditions wherein, $B_{total}$ being set, the variability of $A_{total}$ is negligible, and the sole measurement of the ratio $[A:B]/A_{total}$ gives the possibility of inferring Kd. Thus when $A_{total} < B_{total}$, $[A:B]/A_{total}$ is an excellent approximation of $$\frac{1}{1 + K_d/B_{total}}.$$

Figure 10:
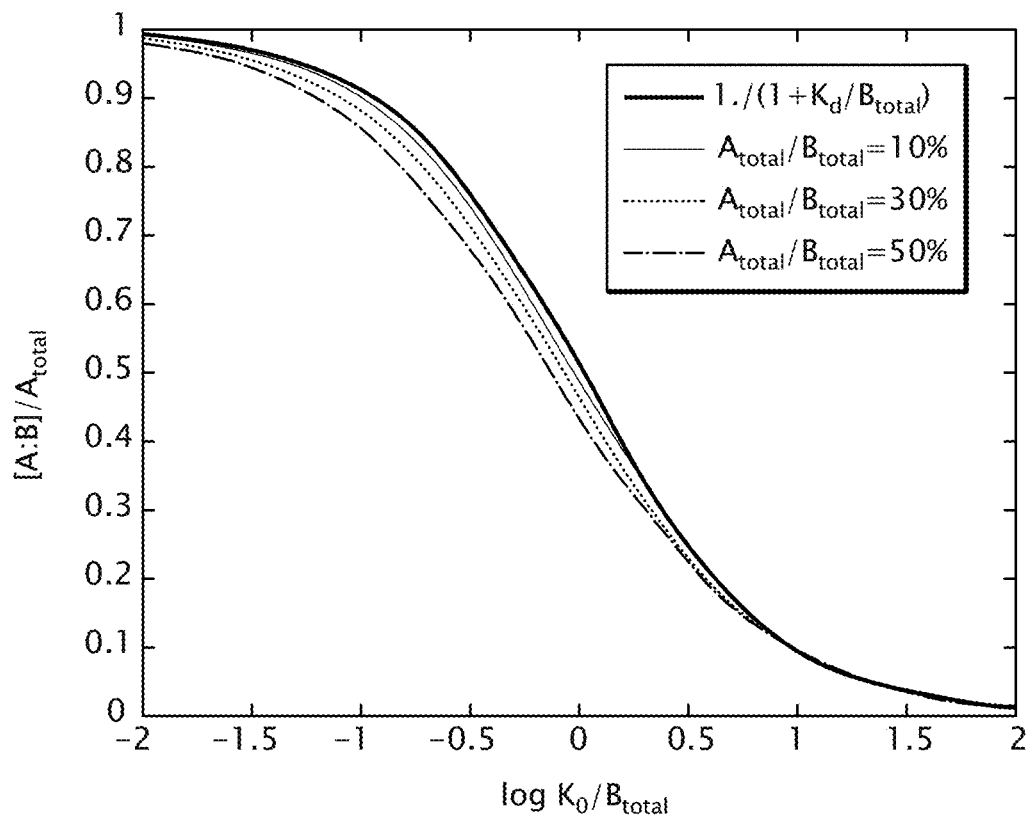
FIG. 10 illustrates the determination of a dissociation coefficient Kd by the method.

FIG. 10 re-presents simulations of the ratio $[A:B]/A_{total}$ is a function of log Kd for different values of the ratio $A_{total}/B_{total}$.

This access to Kd via the ratio $[A:B]/A_{total}$ re-presents a clear advantage for a high flow rate measurement, since so it is possible to evaluate the ratio $[A:B]/A_{total}$ by the ratio of the signaling entity signal 34 which corresponds to the A:B complex over the quantification entity signal which corresponds to $A_{total}$ in the aforementioned particular case.

This ratio may be acquired in real time on the drops and is a criterion for sorting out the drops according to Kd.

The method is applicable for determining the specificity of the target element 37 2 towards diverse signalling entities 34, or the specificity of a molecule or of an assembly of molecules set by the capture element 36 relatively to diverse signalling entities 34. In this case, as Southall signalling entities 34 for example molecules marked with a fluorophores of different colors are injected into the drop 6. It is possible to record simultaneously the signal generated for each signalling entity 34, for example by acquiring fluorescence for different wavelengths. It will thus be possible to determine which signalling entities 34 are localised on the aggregate 10 and to quantify them.

For example, the capture element 36 is the protein G, which captures an anti-body 37 secreted by a cell 90, and the signalling entities 34 are homologous antigens in the different animal species, each marked with a fluorophore of a different color. In this example, the simultaneous measurement of the signal for each signalling entity 34 gives the possibility of determining whether the target element 37 which is the antibody, is specific to an animal species (peak observed on a single color) or not (peak observed on several colors).

In another example, the particles 12 are covered with a sequence of nucleotides able to capture a sequence of complementary nucleotides.

Alternatively, the target element 37 is a protein produced in a drop 6 not comprising any cells but an in vitro translation system.

The method is useful for producing affinity analyses and quantifications of marked products. For example, when the target element is a fusion protein comprising a fluorescent protein like GFP.

The method of further allows the sorting out, the capture and the extraction of the drops having interesting characteristics.

In an example, the method comprises the formation of a sandwich, the target element 37 being on the one hand bound to the capture element 36 of the particle 14 and on the other hand to the signalling entity 34, the signalling entity 34 being fluorescent.

In an example, the capture element 36 is an antibody.

In an example, the signalling entity 34 is an antibody.

In an example, the target element 37 is a protein.

Alternatively, the target element 37 is an antibody or an antibody fragment.

In a particular example, the target element 37 is an antibody and the capture element 36 is a protein G, or a protein A or another protein binding the antibodies, as such as a protein NG or a protein L.

In a particular example, the target element 37 is an antibody and the capture element 36 is an antibody.

In an example, the target element 37 is an antibody and the capture element 36 is an antigen recognized by the antibody.

In another example, the target element 37 is an antibody and the signalling entity 34 is an antigen.

In another example, the capture element 36 consists of a plurality of molecules of captures not identical with each other and the target entity 37 consists of a plurality of molecules not identical with each other.

In another example, capture element 36—target element 37 pairs or capture element 36—target element 37—signalling entity 34 triplets may be analysed simultaneously, either for detecting the presence of several target elements 37 of a different molecular nature, or for detecting and characterizing the presence of different binding sites on a same target element 37.

Figure 24:
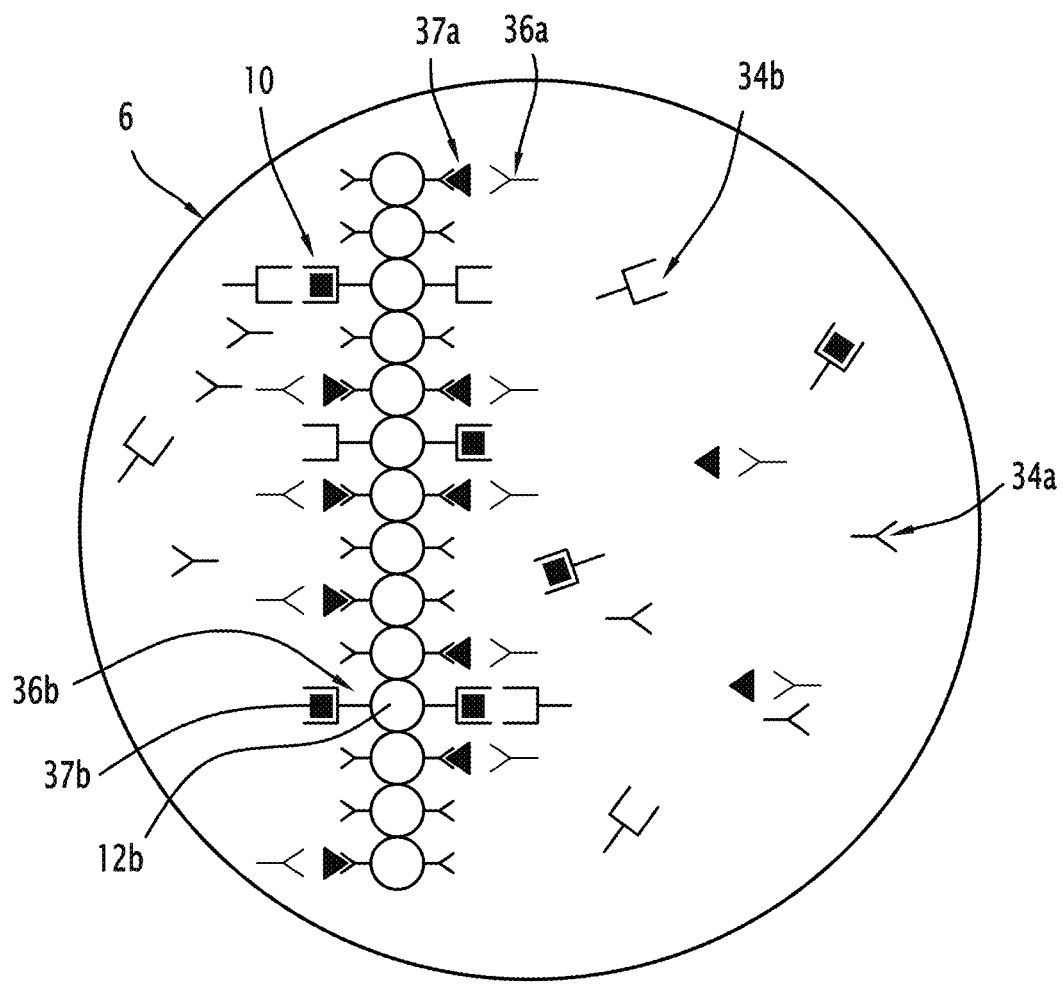
FIG. 24 is a schematic illustration of a drop during a step for applying a method.

For example, as illustrated in the drop in FIG. 24, a drop comprises several target elements 37a, 37b of different nature and several signalling entities 34a, 34b, each being able to form a complex with one of the target elements 37a, 37b. Certain particles 12 of the aggregate 10 comprise a capture element 36a adapted for the capture of a first' target element 37a, other particles comprise another capture element 36b and adapted for the capture of a second target element 37b.

In an example, the method gives the possibility of selecting according to the measured affinities of the immortalized cells secreting antibodies. The selected cells are then again put into cultivation.

In another example, the method gives the possibility of selecting according to the measured affinities of non-immortalized cells secreting antibodies before searching for sequences of genes of the antibodies.

In another example, the method gives the possibility of quantifying cytokines secreted by different types of cells present in the blood.

In certain applications, the aggregation of the particles 12 is reversible.

In certain cases, the presence of the target element 37 makes the aggregation non-reversible and consolidates the aggregate 10 during its formation in the aggregation assembly 30. The aggregate 10 therefore pre-exists in a stable way only in the drops 6 containing the target element 37. In the drops not containing the target element 37, the reversibility of the aggregation of the particles 12 dissolves the aggregate 10 as long as it does not enter the reading area 26. In selected conditions of magnetization and of fluidics, the aggregate 10 can only form and orient itself in the presence of this pre-aggregation, which limits the acquisition of the peak according to FIG. 2 to the drops containing the threshold element 37 by a method other than via the signaling entity 34.

The method is notably applicable for screening antibody producing cells by conducting a measurement of the affinity of the produced antibodies. For example, if the cell is a cell B which may produce antibodies, the affinity of this antibody for at least one antigen is determined by the method according to the invention. And the drops are sorted out by the method according to the invention according to the determined affinity.

In another application, the method gives the possibility of analyzing the secretion of one or several cytokines by a heterogeneous population of white corpuscles. For example, if the cell is a cell which may produce one or several types of cytokines, the cytokines are quantified by the method according to the invention. The result of the analysis is a piece of information on the state of the cell, with a potential diagnostic value.

Examples of application of the method will now be described.

The procedure of the following examples comprises:
the preparation of several aqueous solutions, containing the particles 12, the signaling entity 34 and the target element or advantageously a system capable of producing it in the drops, the injection of aqueous solutions at the inlet of a drop generation chip,
the generation of drops comprising all the reagents of the test,
the incubation of the solution containing the drops,
the injection of the drops in a device according to the invention (two types of devices are described below in Examples 1 and 2),
the measurement of the results of the test,
optionally a sorting out of the drops according to the measurement.

Example 1: Device for Generating Drops and Measuring Drops of Type 1

The production of the drops, called otherwise compartmentalization is achieved after having mixed a solution of reagents and a solution of sample on a chip.

The solutions are kept in ice until compartmentalization in order to avoid any degradation of the reagents and of the samples.

The solution of reagents is sucked up into a tank connected to a Hamilton syringe of 1 mL filled with mineral oil (Sigma Aldrich, #330760) just before starting the compartmentalization.

The samples to be screened are mixed with the work solution just before compartmentalization and then transferred into a glass vial filled beforehand with fluorinated oil (3M, NOVEC HFE-7500) and the vial is maintained at 4° on ice.

Capillaries, advantageously in PTFE with an inner diameter of 0.3 mm (sold by Fischer, #11919445) give the possibility of connecting the vial and the tank of the solution of reagents to the device for forming the drops.

Both of these solutions are injected on a chip for forming drops which gives the possibility of generating drops comprising an equal volume of each of both solutions.

The volume of the drops is selected by the user from the flow rate of the fluorinated oil. Advantageously, the volume of the drops is 33 picoliters. The fluorinated oil is the carrier fluid 8. It forms the continuous phase of the emulsion comprising the drops.

The solutions of test reagents and of test samples to be screened are injected into the chip with the same flow rate, advantageously at 200 microliters/hour for each solution. The flow rate is improved by a standard syringe pump system for example a pump neMESYS from Cetoni or by a pump controlling the pressure for example the system marketed by Fluigent.

The drops are generated at a hydrodynamic focussing junction as illustrated in FIGS. 11 and 12. The external phase is here a fluorinated oil (3M, NOVEC HFE-7500) at which are added two % weight/volume of surfactants (for example a three-block copolymer comprising two perfluoropolyether (PFPE) tails (with a molecular weight of about ~6,000 g/mol) and a PEG head (~600 g/mol)).

FIG. 11 and FIG. 12 represent flow focussing devices giving the possibility of mixing a flow containing the magnetic beads mixed with the other reagents and a flow containing the samples before the formation of drops at the hydrodynamic focussing junction located on the right. In FIG. 11, the magnetic particles measure 500 nm in diameter and in FIG. 12 the magnetic particles measure 200 nm in diameter.

A second step is the collection step. A vial maintained at 4° under the magnetic filed, advantageously generated by a ring-shaped magnet (Amazing magnet H250H-DM), allows collection of the drops. A short capillary gives the possibility of connecting the vial to the chip. Ideally, the output capillary measures less than 20 cm, advantageously 10 cm.

The drops are set to incubate advantageously at 37° C. for 20 to 90 minutes and under magnetic fields, the time and the incubation temperature depending on the conducted analysis and on the type of producing entity 90 and of target element 37 investigated.

Subsequently to the incubation, the vial containing the emulsion is transferred at 4° always maintained under a magnetic field.

The first type of device, is a device according to the invention as described in FIG. 1.

The vial containing the drops is connected to a chip for reinjection, the vial is on the one hand connected to the chip and on the other hand to a pressure system, a pressure pump or a syringe and its pump, forming the circulation assembly 22.

The spacing apart assembly 31 comprises two oil inlets connected to the chip. These inlets are intended to inject oil advantageously fluorinated oil giving the possibility of spacing apart the drops of the emulsion as illustrated in FIG. 13.

The spacing apart oil flow rates are advantageously each set to 300 microliters/hour as well as the flow rate of the circulation assembly is advantageously set to 50 microliter/hour and give the possibility of adjusting the flow rate and the reinjection frequency of drops so as to obtain a frequency comprised between 250 and 1,000 Hz.

A pair of permanent magnets 38 advantageously provided by K&J Magnetics, #BC 14-N52, is placed on either side of the chip around the main channel 24. These magnets 38 are intended to generate and orient the bead aggregates during the reinjection of the drops.

A piece of software for controlling the equipment, for example lasers or photomultipliers, is generated for analyzing and sorting out the drops. The sorting system requires an FPGA card for conducting an analysis in real time of the signal.

The measurement is carried out in the drops one by one after their passing into the spacing apart assembly and these drops may be sorted out towards a desired outlet after a reading area illustrated in FIG. 14.

When a sorting out and a recovery are desired, the sorted drops and the non-sorted emulsions are collected on ice and the contents of the drops is recovered from standard procedures.

Example 2: Device for Measurement of Drops of Type 2

The second type of measurement device is a camber for storage of drops produced in a 2 dimensional plane. This example has two possible alternatives for making such chambers.

The first is a chamber made by conventional micro-manufacturing in PDMS, advantageously comprising pillars positioned in a regular way in order to avoid the collapse of the chamber as illustrated in FIGS. 3 to 6.

Figure 16:
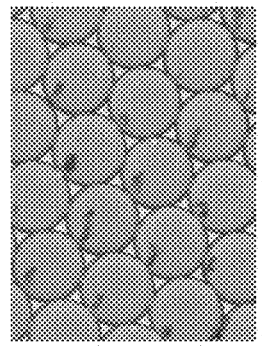

The second is a glass chamber according to the invention PCT/FR2009/051396 as illustrated in FIGS. 14 and 16. Advantageously, this approach gives the possibility of carrying out an incubation of the drops over long periods (>1H) without deforming the drops. The drops may therefore be directly collected in such a chamber after their formation.

Figure 15:
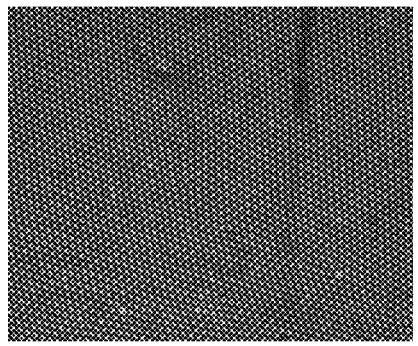
FIGS. 15 and 16 illustrate assemblies for reading in two dimensions.

FIG. 15 and FIG. 16 illustrate an example of a readout device in two dimensions according to the invention, here in a glass chamber, the magnetic field is handled by a permanent magnet located on one side of the chamber.

General for the Following Examples

In the following examples, the preparation of the drops comprises:
the preparation of two aqueous solutions, called "reagent solution" containing the particles 12, the signaling entity 34 and the "sample solution to be screened" containing the target element in the examples below,
the injection of both aqueous solutions at the inlet of the chip for generating drops,
the generation of drops comprising an equal volume of each of both solutions,
the measurement of the drops in a device of type 1, optionally the sorting out of the drops (Example 4).

The preparation of both aqueous solutions will be described in general and the differences relatively to this standard procedure will be mentioned in the Examples if required.

a) Preparation of the Reagent Solution.

The elements comprised in this solution are advantageously inert towards each other in order to avoid aggregations of reagents before generating the drops.

This first aqueous solution contains:
particles 12 which are here colloidal magnetic particles, functionalized with a capture element 36, here a protein G, and
a signaling entity 34 which here is an antigen marked with fluorescence, for example an antigen marked with the fluorophore Alexafluor488,
a coloring agent giving the possibility of detecting the drops 6 for example sulforhodamine B,
an entity for quantifying antibodies, which here is fluorescent, for example a fragment of a anti-mouse monoclonal antibody marked with the fluorophore Alexafluor647, a working solution.

The concentrations of each reagent will be detailed with regard to each example.

These reagents are diluted in a solution called a working solution. The working solution for example comprises:
30% v/v percoll (provided by Sigma Aldrich),
50 mM of NaCl,
25 mM of HEPES buffer at pH 7.4,
0.1% v/v of Pluronic F-68 provided by Life Technologies,
5%-v/v of Serum Super low IgG from Thermo Scientific.

The volume of the working solution is completed with RPMI-1640 supplemented with Glutamax provided by Life Technologies in order to attain the final volume.

The 12 magnetic colloidal particles are treated before use. The particles 12 are particles provided by Chemicell (ScreenMAG) or Ademtech (Bio Adembeads) in a storage solution. They are retained on a magnetic support in order to suppress the storage solution but they are suspended in an excess of Pluronic F-127 at 10% w/w (Sigma Aldrich), advantageously 10× the initial volume of particles, and incubated for thirty minutes at room temperature.

After this treatment, the magnetic colloidal particles 12 are washed twice in PBS and suspended in the working solution.

Advantageously, the particles 12 suspended in the working solution are subject to sonication for ten minutes before adding the test reagents.

The fluorescent reagents are treated before use. The fluorescent reagents are for example, the signaling element 34, the detection coloring agent of the drop and the quantification reagent. The fluorescent reagents are centrifuged for five minutes at at least 12,000 G and at 4° C. before suppressing the traces of aggregates of reagents.

b) Preparation of the Sample Solution to be Screened.

The sample solution to be screened comprises:
a target element 37 able to be captured by the capture element 36,
or a productive entity 90 which may synthesize this target element 37 in the drop during an incubation phase. This system may for example be a cell, or a DNA or an expression system in vitro. In this case, the target element 37 does not pre-exist in the sample solution to be screened.
a working solution.

The concentration of cells to be used depends on the desired size for the drops. Advantageously, the concentration of cells per drop is of 0.3 cells per drop. An emulsion with drops of 33 picoliters contains more than 30·10⁶ drops per milliliter. For drops of 33 picoliters, in order to have 0.3 cells per drop, 18·10⁶ cells per milliliter of concentration in the sample solution to be screened are approximately required (which is concentrated twice relatively to the drops).

It should be noted that the concentration of cells in the sample solution to be screened is twice greater than the final concentration since both aqueous solutions will be mixed in a drop with a 50/50 ratio.

The preparation procedure of the cells depends on the cell type and on the goal of the experiment.

Example 3: Quantification and Measurement of Affinity of a Monoclonal Antibody for its Antigen In this example, the target element 37 is an antibody which is already contained in the solution to be screened, this example does not apply cells.

An object of this example is to demonstrate the possibility of a binding test with several colors. Another object is to demonstrate the possibility of normalizing a re-localization signal with another signal. This gives the possibility of evaluating the $K_d$ from a localization signal of an antigen (signaling entity) by giving the possibility of normalization by the signal of the protein for lightweight chain binding to the re-localized antibody (quantification entity).

In this experiment, the drops measure 33 picoliters.

The sample solution to be screened contains different concentrations of anti-hTNFα monoclonal antibodies (provided by Sigma Aldrich T6817) diluted in RPMI-1640 with 2 mM of glutamax supplemented with 30% v/v Percoll, 0.1% v/v Pluronic F-68, 18 mM of HEPES.

The anti-hTNFα monoclonal antibody concentrations in the sample solution to be screened are the following: 0 nM, 10 nM, 25 nM or 50 nM.

The solution of reagents contains the following reagents:
  8.33% v/v of magnetic particles (Ademtech #0433)
  200 nM of Fab-DL650 anti-mouse Fab'2 (quantification entity),
  100 nM of hTNFα-AF488 (signaling entity),
  1 μm of sulforhodamine B (for marking the drops).

The antibody Fab-DL650 fragment is prepared from Goat F(ab')2 anti-Mouse IgG (Fab')2 conjugated with DyLight-650 (marketed by Abcam, ab98760), digested with Papain and purified on a column of protein G.

This solution is completed with RPMI-1640+2 mM of Glutamax supplemented with 30% v/v Percoll, 0.1% v/v Pluronic F-68 and 18 mM of HEPES.

This gives the possibility of obtaining four different emulsions with 50 nM of antigen-AF488, 100 nM of Fab-DL650 and respectively 0 nM, 5 nM, 12.5 nM or 25 nM of monoclonal antibodies directed against the antigen.

The drops are then analyzed by means of a device of type 1.

Figure 17:
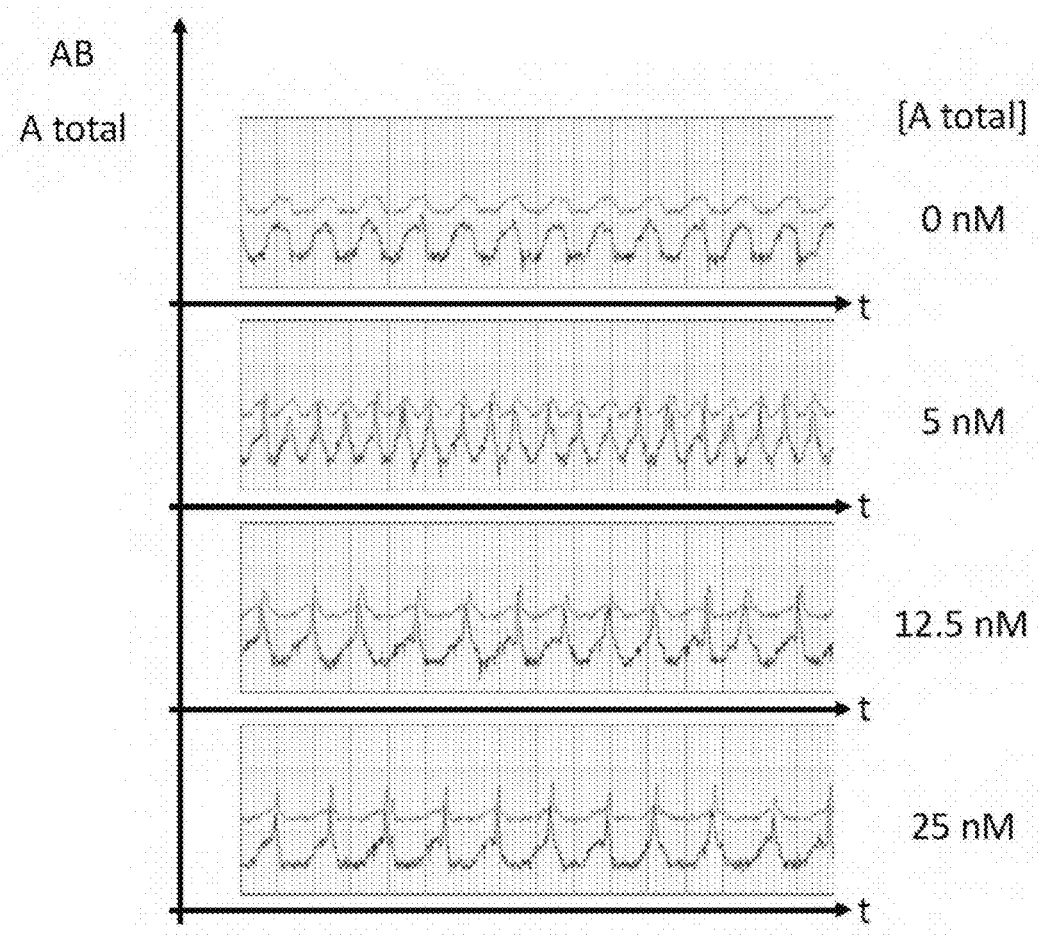
FIGS. 17, 18 and 19 illustrate example 3.

This experiment gives the possibility of showing the possibility of conducting a binding test on magnetic particles in a column in the drops with two fluorescence readouts of secondary reagents, as this is illustrated by FIG. 17. Further, this approach gives the possibility of characterizing the binding affinity by correlating the binding signal of the antigen to the amount of antibody involved in the capture of the antigen. Indeed, a parameter independent of the concentration of antibodies may be extracted from the analysis.

Figure 19:
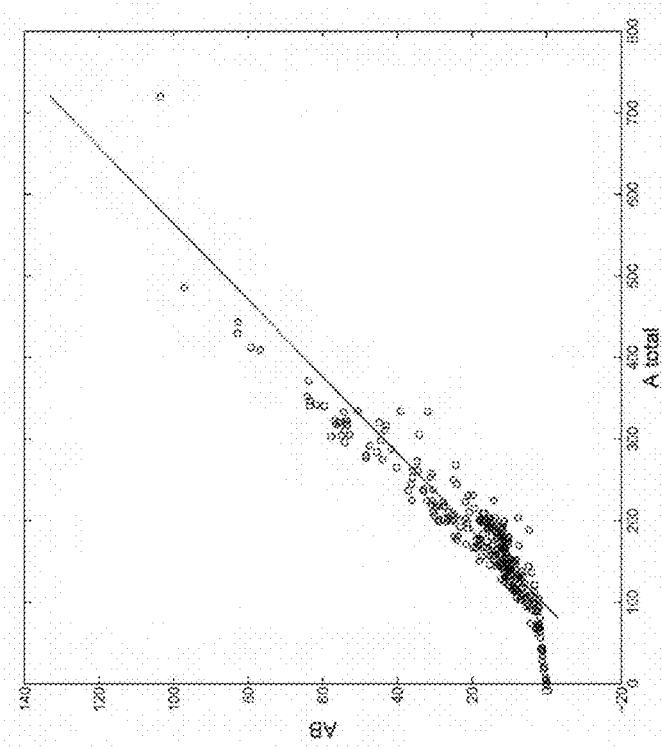
Figure 18:
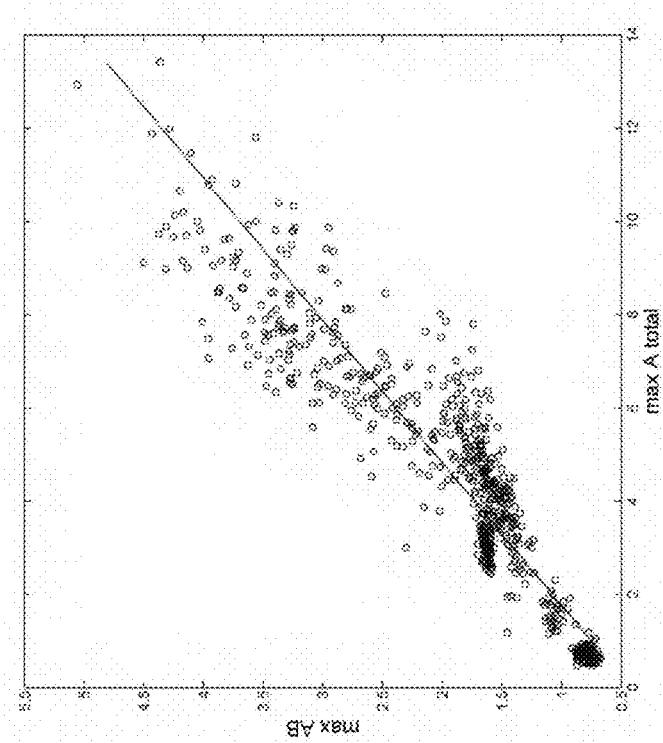

FIG. 17 illustrates a real time fluorescence measurement on a trail of drops for two colors, one corresponding to the signaling entity 34 (complex AB, pale gray in FIG. 17) and one corresponding to the quantification entity, (compound A, dark gray), and for increasing amounts of A from 0 to 25 nM. FIG. 18 is a two-dimensional graph corresponding to this experiment, wherein each point is an abscissa drop for the fluorescence maximum for the color of the quantification entity, and in ordinates the fluorescence maximum for the signaling entity 34. FIG. 19 represents for the same set of drops a two-dimensional graph wherein each point has for an abscissa the integral for the color of the quantification entity, and in ordinates the integral for the signaling entity 34.

We see that the relationship between the "maximum" signals is globally linear in spite of a dispersion of the data points (as suggested by the linear regression with $R^2=0.79$), due inter alia to fluctuations in shape and in position of the aggregate over the whole of the drops. We see that the relationship between the "integral" signals is characterized by a linear regression with a better $R^2$ ($R^2=0.90$), the dispersion of the points is much lower and gives the possibility of estimating the Kd from the AB/A ratio as explained earlier.

Example 4: Sorting Out of Hybridomas at the Scale of the Single Cell Depending on the Affinity of the Antibodies which they Secrete The object of this experiment is to demonstrate the screening of antibody producing cells according to binding affinities of the secreted monoclonal antibodies by using reagents and an approach similar to Example 3. In particular, it is seen that it is possible to differentiate and sort out two hybridomas: a hybridoma secreting an anti TNF alpha (25H12 line) antibody and a hybridoma secreting an anti c-Myc antibody (line 9E10).

In this example not only the affinity is estimated but further the cells are sorted out according to their affinity.

In the experiment, the drops measure 33 picoliters.

The sample solution to be screened contains 13.5·10⁶ hybridoma 9E10 cells and 4.5 10⁶ hybridoma 25H12 cells suspended in the working solution described in example 1.

The solution of reagents contains the following reagents suspended in the working solution:
  8.33% v/v of magnetic particles (Ademtech #0433),
  100 nM of antibody-DL650 anti-Mouse Fab'2 fragments (quantification entity),
  100 nM of hTNFα-AF488 (signaling entity),
  2 μm of sulforhodamine B.

This results in an emulsion with 50 nM of hTNFα-AF488, 50 nM of Fab-DL650 and single hybridoma cells secreting antibodies either directed against HTNFα for the 25H12 hybridomas or against the c-Myc for the 9E10 hybridomas. The 25H12 cells represent 25% of the cells and the 9E10 cells represent 75% of the cells.

The fluorescence is measured for the different fluorescence channels, in green for the antigen, and in red for the quantification entity. The relevant signal in this example is the fluorescence maximum. The drops exhibiting a significant green and red fluorescence signal are sorted out and collected.

The sorted out and collected drops are broken and the cells are recovered as described in Mazutis et al. (Nat prot 2013).

Figure 20:
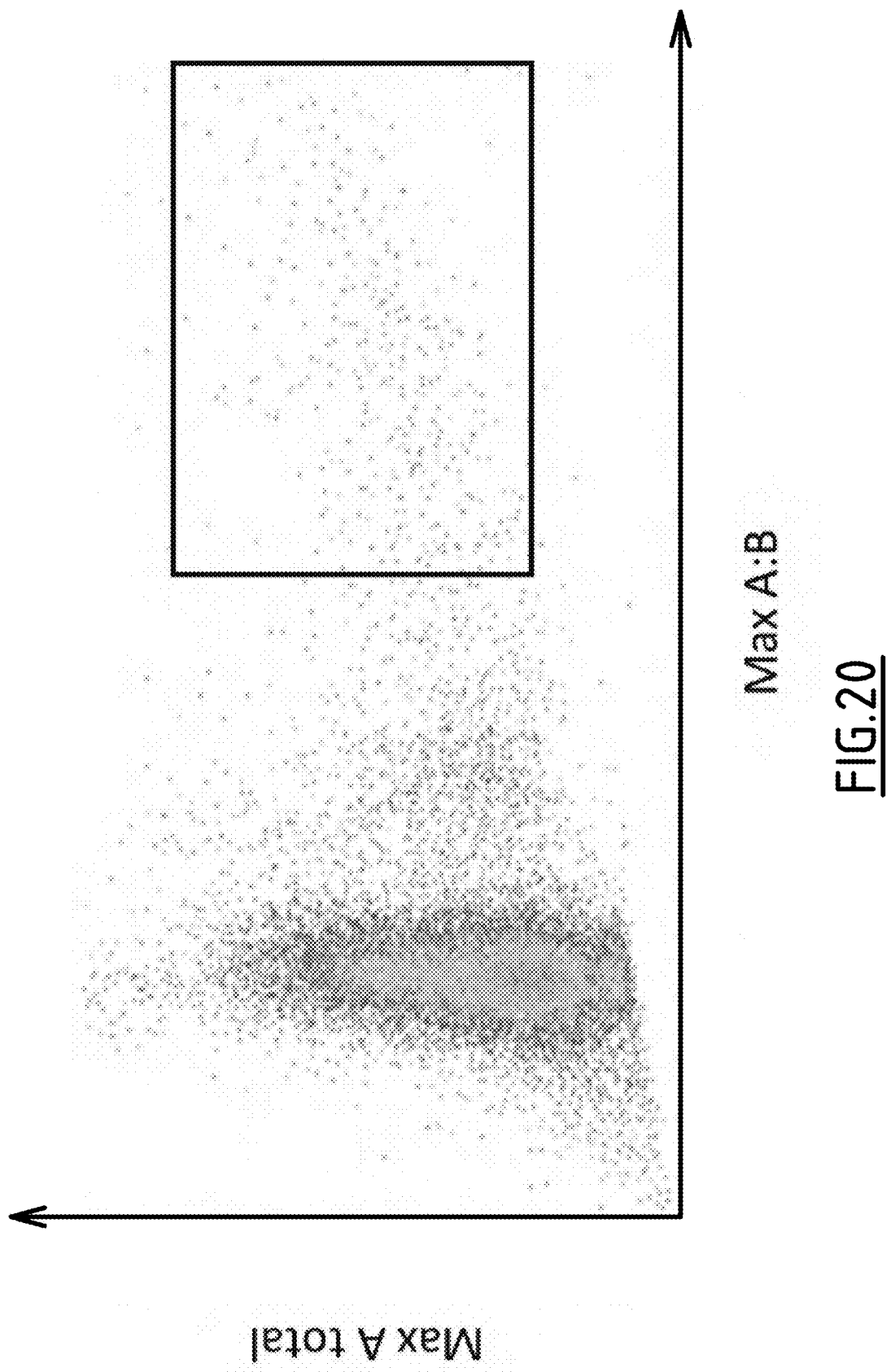
FIGS. 20 and 21 illustrate example 4.
Figure 21:
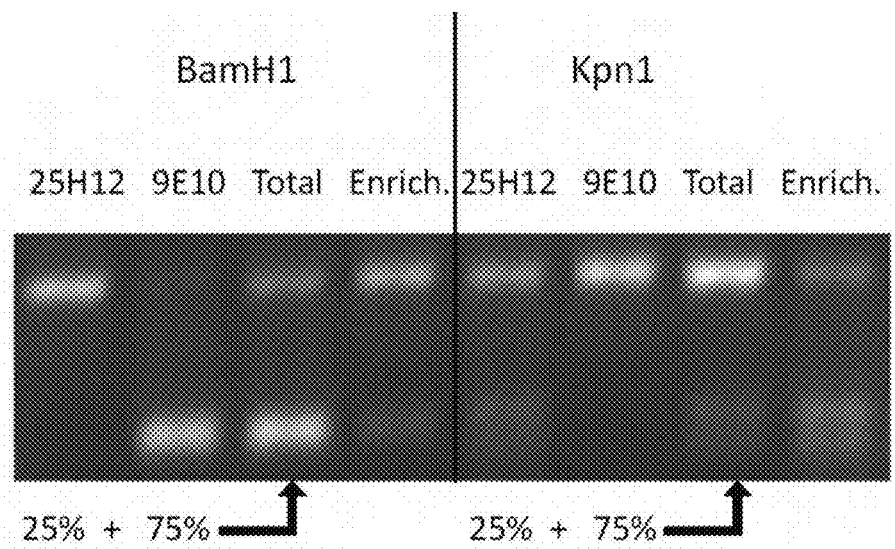

A real time PCR is then carried out on the solutions of cells extracted from the sorted out drops or from the non-sorted out emulsion, and the PCR products are digested by using two restriction enzymes. The BamHI enzyme has a restriction site on the DNAc from the 9E10 cells and the KpnI enzyme has a restriction site on the DNAc stemming from 25H12. The digestion products are analyzed by electrophoresis. In FIGS. 20 and 21, it is seen that the method allows an enrichment in 25H12 cells after screening by the device.

The invention therefore gives the possibility of specific selection with a high flow rate of single cells secreting antibodies recognizing the signaling entity.

FIG. 20 and FIG. 21 illustrate a sorting out of hybridomas according to the invention. FIG. 20 represents a graph in two dimensions wherein each point is an abscissa drop of the fluorescence maximum for the color of the signaling entity, and in ordinates the fluorescence maximum for the quantification entity. The black window indicates the selected range of values for carrying out the sorting.

FIG. 21 illustrates an analysis by real time PCR and enzymatic digestion by BamH1 (on the series of the four left columns) or Kpn1 (on the series of the four right columns) from the DNA of the pure hybridomas 25H12 (anti TNF alpha) and 9E10 (anti cMyc) (on the first two columns of each series), and in a 25/75 mixture (on the third column of each series) and finally after enrichment of this mixture according to the invention with a biotest for recognizing the TNF alpha (on the fourth column of each series). There is an enrichment by a factor of about 20 in 25H12 cells after the sorting out.

Example 5: Quantification of Cytokine Secreted at the Scale of the Single Cell

The object of this example is to demonstrate the possibility of detecting and quantifying a cytokine secreted at the scale of the single cell with a generic approach of sandwiched immunological tests. In this example the capture element 36 is a biotinylated antibody attached to streptavidin and the signaling entity 34 is a fluorescent detection antibody.

The particles are functionalized with streptavidin and the capture antibodies are biotinylated. It is possible to use another method for coupling the capture antibody on the particles.

The coupling method is covalent or not covalent. The important criterion is that the signaling entities are not directly captured at the surface of the particles.

A method is shown here for quantifying the secretion of gamma interferon (IFNγ), a biomarker cytokine in many cases of inflammation or infection, at the scale of the single cell, according to the invention and with a measurement device of type 1. Such a biological assay may be used for testing the operation of the immune system of patients within the scope of functional immunology tests. In such tests, the immune cells are stimulated and their cytokine secretion is measured.

In this example, we demonstrated the possibility of assaying recombinant IFNγ in drops with a volume measuring 25 to 40 pL.

But in fine, this assay has the purpose of being used for cells individually encapsulated, and the general procedure to do this is now described.

Each drop contains all the elements required for the immuno-sandwich system: the sandwich for example consists of magnetic fluorescent beads covered with streptavidin, of biotinylated antibodies and of fluorescent antibodies. Both kinds of antibodies are directed against two different epitopes of IFNγ.

The working solution contains some culture medium and cell activators (for example mitogens, antigens).

Once the cells and the immuno-test sandwich system are encapsulated into the drops, the emulsion is incubated. Under the action of the magnetic field, the particles are oriented within the drop and form a column. In the case of a non-covalent coupling of the capture antibody by a streptavidin-biotin system, the aggregation of the beads in a column is made irreversible by bridging the beads via the multiple biotins located on the capture antibody.

The incubation allows secretion and optionally the binding of the molecules with each other. After the incubation, the drops are analyzed by means of the device of type 1 according to the invention.

The drops comprising cells do not respond to the activation signal and do not secrete any gamma interferon, include fluorescent antibodies within the whole drop. The drops secreting gamma interferons have biotinylated capture antibodies—IFNγ—fluorescent detection antibodies sandwiches which are re-localized on the streptavidin surface of the beads. In these drops, a re-localized fluorescence at the aggregate is therefore measured.

The more gamma interferons are secreted, the more the fluorescence is on the line of particles and the higher is the fluorescence peak and/or the integral of the fluorescence signal are. This therefore gives the possibility of quantifying the gamma interferons secreted by the stimulated cells.

In this example, we have shown that it is possible to achieve a test for detecting and quantifying the gamma interferon according to the invention by using the following reagents:

Solution of reagents:
A biotinylated capture antibody (Mabtech 7-B6-1) at 200 nM.
A detection antibody marked with phycoerythrin (PE) (Miltenyi 45-15) at 200 nM (signaling entity)
Working solution: 30% Percoll (Sigma)/1% Pluronic F-68 (LifeTech)/69% PBS (Sigma)
The solutions to be screened:
0 or 20 or 200 nM of recombinant IFNγ 1B (Miltenyi)
Magnetic beads screenMAG/R Streptavidin 0.5 µm (Chemicell) (20 µl for 120 µl of emulsion).

A device similar to the one of Example 1 and 3 is used for generating drops from the three solutions to be screened, by acting on the flows so as to obtain a different size for each IFNγ concentration (but always by retaining the two injection flows of the aqueous solutions equal in order to obtain the desired final concentration). The drops are of about 25 pL for 0 nM of IFNγ, 31 pL for a final 10 nM, and 38 pL for a final 100 nM. These three populations of drops are mixed, incubated and analyzed in order to measure the re-localization of the orange detection antibody. The identical procedure is the one of Example 3. The fluorescence is measured for 2 fluorescence channels: orange for the detection antibody (PMT3), red for the beads (PMT4). The signal considered in this example is the fluorescence maximum.

We have removed from the analysis the drops for which the values on the PMT4 (beads) are low (PMT4<0.34), which corresponds to the case when the line of magnetic beads is poorly formed or oriented.

Figure 22:
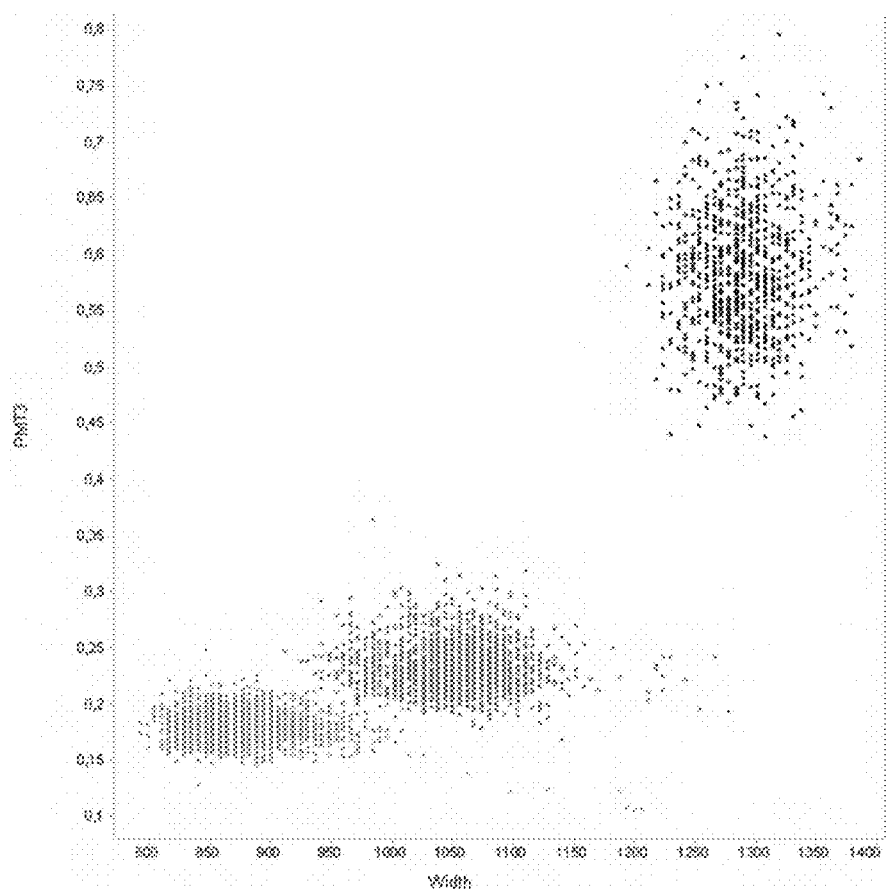
FIGS. 22 and 23 illustrate example 5.
Figure 23:
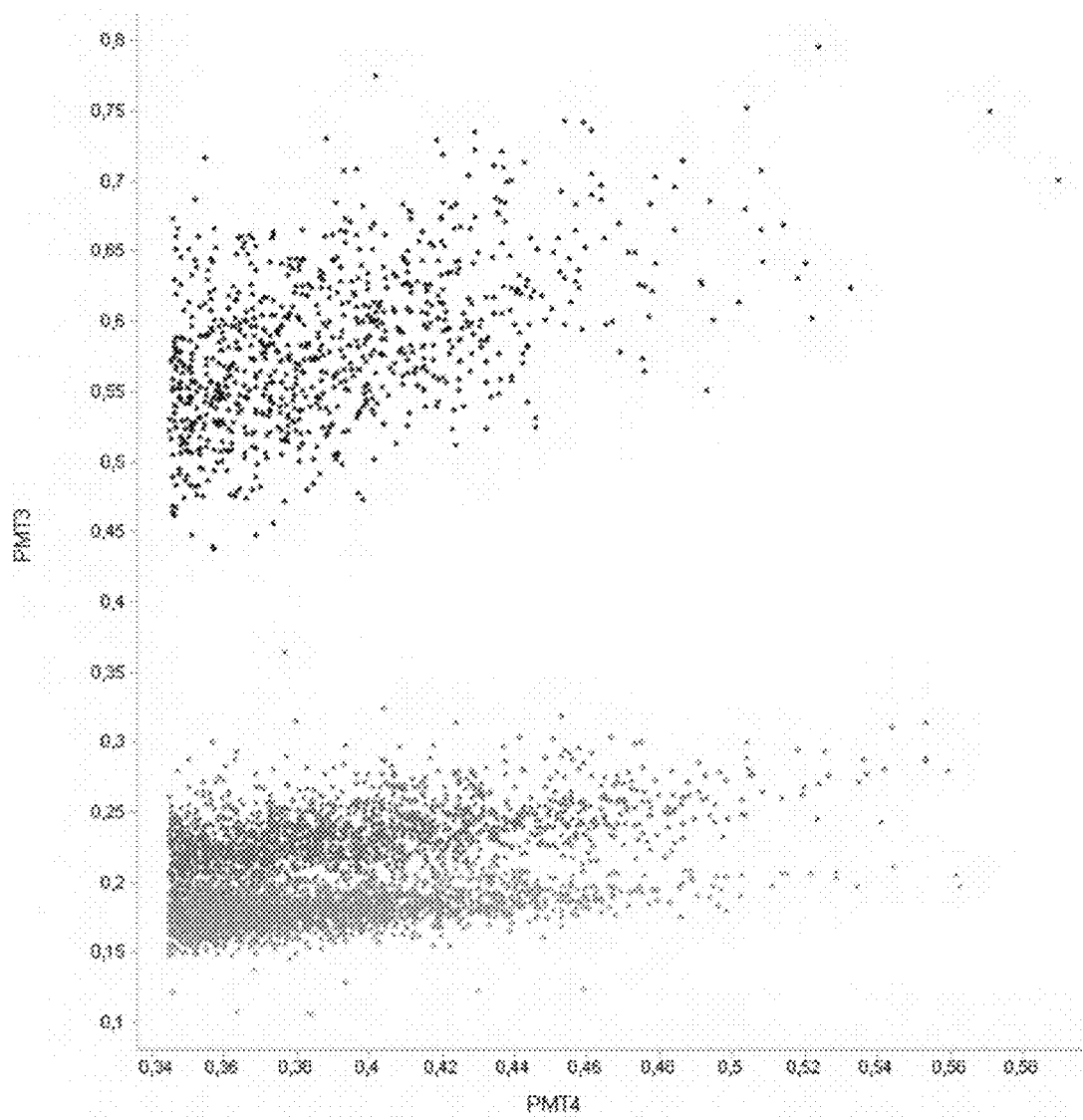

The analysis of the remaining drops shows that it is possible to discriminate the 3 populations of drops in size and in detection antibody signal (PMT3), which demonstrates the possibility of quantifying the IFNγ in the drops as illustrated by FIG. 22 and by FIG. 23.

It also shows a linear relationship between the signal on PMT3 and PMT4, which suggests that the amount of detection antibody per magnetic bead is constant and that the variation of the signaling entity signal (PMT3) is directly correlated with the variation in the shape of the aggregate.

FIG. 22 and FIG. 23 illustrate a detection and quantification of a cytokine (gamma interferon, IFNγ) in microfluidic drops according to the invention. In FIG. 22, the three populations of drops containing 0, 10 or 100 nM of IFNγ are represented according to their maximum fluorescence in orange (PMT3), which corresponds to the detection antibody, relatively to their size (Width). The three populations of drops are illustrated in FIG. 23 according to their maximum fluorescence in orange (PMT3), relatively to their maximum fluorescence in red (PMT4), which corresponds to the beads.

Example 6: Sorting Out of Primary Cells, More Specifically of Lymphocytes B (Plasma Cells) at the Scale of the Single Cell According to the Binding Activity of the Antibodies which they Secrete The object of this experiment is to demonstrate the screening of primary cells producing antibodies according to the binding activity of the secreted monoclonal antibodies by using reagents and an approach similar to Example 4. In particular, it is shown that it is possible to differentiate and sort out lymphocytes B according to the binding activity of the monoclonal antibodies which they secrete.

The lymphocytes B having been extracted beforehand from the spleen of a mouse and purified according to a standard procedure (Pan B kit II #130-104-443, Miltenyi Biotec). In this example, the capture element 36 is a biotinylated antigen, more specifically "TTbiotin", the protein Tetanus Toxoid functionalized beforehand with a biotin by means of a procedure for marking a standard kit for example provided by ThermoFisher. In this example, only the binding activity of the antibody to the target antigen is observed but in addition the cells are sorted out according to their binding activity.

In the experiment, the drops measure 40 picoliters.
In this example, the working solution comprises:
5%-v/v Serum Super low IgG (#SH30898.03, Thermo Thermo Scientific,
25 mM of HEPES buffer at pH 7.4,
0.1% v/v Pluronic F-68 provided by Life Technologies,
1% v-v Antibiotic-Antimycotic (#15240, ThermoFisher).

The volume of the working solution is completed with DMEM-F12 provided by Life Technologies in order to attain the final volume.

Two emulsions are produced and put in common after production and before analysis and screening. The majority emulsion (~10 Million drops) consists of the cells to be screened as well as of the detection reagents. The second emulsion, a so called negative control emulsion, comprising ~1 Million drops, consist only of detection reagents. Both emulsions are differentiable by means of the use of two different concentrations of an orange fluorophore, sulforhodamine B.

The sample solution to be screened contains $6.6 \cdot 10^6$ purified primary cells suspended in a working solution as described in example 1.

The solution of reagents contains the following reagents suspended in the working solution:
33.33% v-v of magnetic particles Streptavidin (Ademtech #0433),
200 nM of Rabbit Fab'2 anti-FCmouse AF647, JacksonIR #315-606-146 (quantification entity),
100 nM of TTbiotin (capture element 36),
0.8 or 1.6 or 2.4 µM of sulforhodamine B (Sigma Aldrich #S1402).

This results in an emulsion with 50 nM of biotinylated antigen (TTbiotin), 100 nM of Rab.Fab'2.antiFCmouse AF647 and unique primary cells either secreting or not antibodies directed against the antigen (Tetanus Toxoid).

The fluorescence is measured in red for the quantification entity. The signal considered in this example is the fluorescence maximum. The drops having a large red fluorescence signal, having the right size and stemming from the emulsion of the primary cells (low orange fluorescence of the sulforhodamine B) are sorted out, collected and broken and then the cells are recovered like in example 4.

Figure 25:
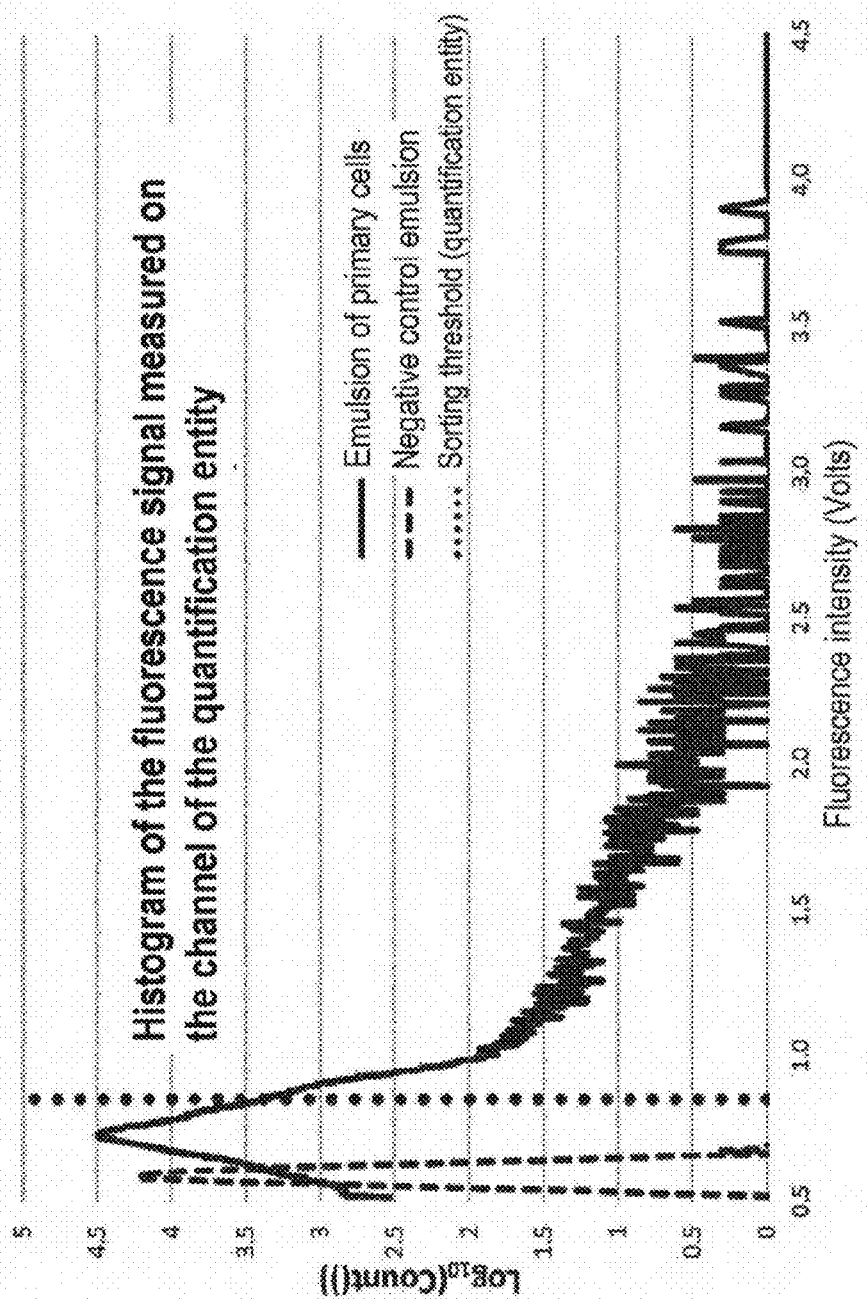
FIG. 25 illustrates example 6.

FIG. 25 represents a histogram of the number of drops counted for a fluorescence signal measured on the channel of the quantification entity. The abscissa represents the fluorescence maximum for the color of the quantification entity, and the ordinate represents the logarithm in base 10 of the number of drops measured at this fluorescence value. The values obtained for the emulsion of primary cells to be screened are plotted in a black solid line. The values obtained for the negative control emulsion are plotted in a gray dotted line. The vertical line of the points with black circles indicates the threshold value above which the drops are selected for the sorting.

An ELISpot is then achieved on the solutions of cells extracted from the sorted out drops or from non-sorted out cells, i.e. after purification (kit Miltenyi) but before microfluidic screening. The thereby analyzed cells by ELISpot are tested both for the secretion of antibodies and for the secretion of an anti-TT antibody.

An analysis by ELISpot of sorted out primary cells and of purified but non-sorted primary cells is achieved. The analysis is carried out on two markers by using procedures as described in the kit Mouse IgG ELISpot$^{BASIC}$ (Mabtech #3825-2A). The first, a so called IgG, uses the "Total Ig ELISpot" procedure and gives the possibility of detecting the number of cells secreting antibodies. The second, a so called TT, uses the "Antigen-specific Ig ELISpot, PROTOCOL II" procedure and allows detection of the number of cells secreting antibodies having a binding activity against the antigen TT.

The enrichment η is calculated according to the following formula, $N_{+,0}$ being the number of positive cells before sorting out, $N_{+,1}$ being the number of positive cells after sorting, $N_{-,0}$ and $N_{-,1}$ being the respective values of negative cells before and after sorting.

$$\eta = \frac{N_{+,1}}{N_{-,1}} \bigg/ \frac{N_{+,0}}{N_{-,0}}$$

In an experiment, for 5,000 non-sorted cells, 51 positive cells to TT and 4,949 negative cells are obtained and for a 1,000 sorted cells, 132 positive cells to TT and 868 negative cells are obtained.

The experiment shows an enrichment q of a factor of about 15 in secreting cells having a binding activity to TT after the sorting and these cells represent 93% of the detected cells secreting antibodies.

The test ELISpot gives the possibility of showing that the method allows enrichment in primary cells before the screening with the device.

The invention therefore allows a specific selection at a high flow rate of single primary cells secreting antibodies recognizing the capture element.

Example 7: Quantification of a Monoclonal Antibody and Detection of Binding with its Antigen in a 2D Chamber In this example, the target element 37 is an antibody which is already contained in the solution to be screened, this example does not apply cells.

An object of this example is to demonstrate the possibility of measuring a quantitative response according to the concentration of a monoclonal antibody for a given antigen in a device of type 60, i.e. a chamber in which the drops are distributed in two dimensions in a single layer. In this example, the signaling entity is a fluorescent antigen, more specifically "TT-AF488", the protein Tetanus Toxoid functionalized beforehand with a fluorophore AlexaFlour-488 by means of a marking procedure of a standard kit for example provided by ThermoFisher. In this example, the magnetic particles used for forming the columns of drops are marked with saturation with the capture entity, here the "CaptureSelect™ Biotin Anti-LC-kappa (murine) conjugate" (ThermoFisher #7103152500).

In this experiment, the drops measure 40 picoliters.
In this example the working solution comprises:
- 5%-v-v Serum Super low IgG (#SH30898.03, Thermo Thermo Scientific),
- 25 mM of HEPES buffer at pH 7.4,
- 0.1% v/v Pluronic F-68 provided by Life Technologies.

The volume of the working solution is completed with DMEM-F12 without any phenol red provided by Life Technologies for attaining the final volume.

The solution of reagents contains the following reagents suspended in the working solution:
- 33.33% v-v of magnetic particles Streptavidin (Ademtech #0433), marked beforehand with saturation with the capture entity,
- 150 nM of Rabbit Fab'2 anti-FCmouse AF647, JacksonIR #315-606-146 (quantification entity),
- 50 nM of TT-AF488 (capture entity),
- 0.8 or 1.6 or 2.4 µM of sulforhodamine B (Sigma Aldrich #S1402).

This results in an emulsion with 25 nM of fluorescent antigen (TT-AF488), 75 nM of quantification entity (Rab.Fab'2.antiFCmouse AF647) and a concentration range of a monoclonal antibody, having a binding activity against the antigen (TT7), comprising the following values: 0; 4.2; 12.5; 20.8; 42 (only Fig. S7b); 62.5; 83.3; 125; 208; 250 (only Fig. S7b). The anti-TT antibody, a so called TT7, was obtained by expression of a recombinant protein from the sequence published in the article written by Brandon J DeKosky et al., entitled "High-throughput sequencing of the paired human immunoglobulin heavy and light chain repertoire" published in Nature Biotechnology of Volume 31, pages 166 to 169 in 2013.

The measured multiple emulsions are differentiable by the use of a range of concentrations of an orange fluorophore, sulforhodamine B. The collected measurements were not achieved simultaneously.

Figure 26:
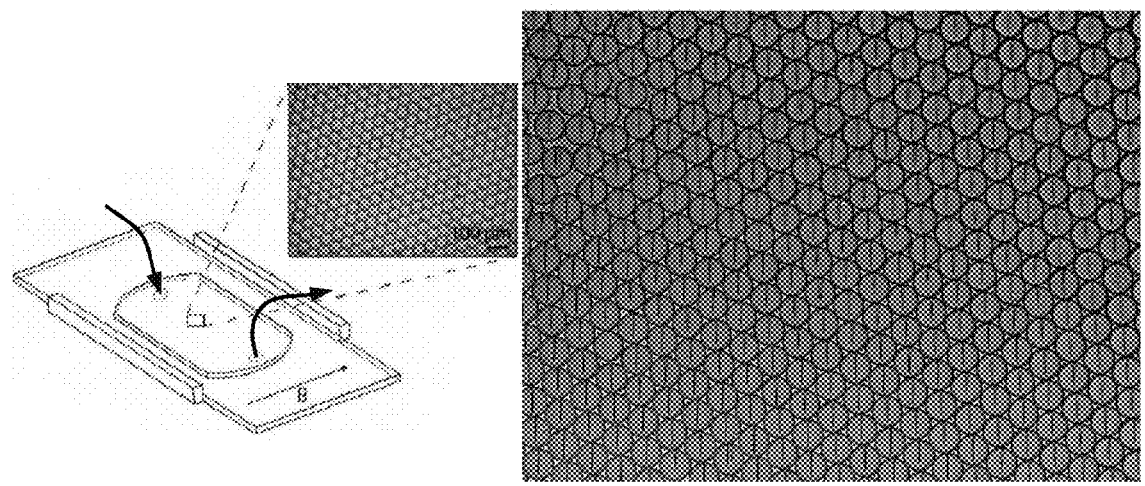
FIGS. 26, 27 and 28 illustrate example 7.

FIG. 26 represents the measurement device of the type of the second apparatus 60 used in this example. A chamber with a height of 40 µm is created between two glass slides. An inlet and an outlet are made on the upper glass slide and each provided with a standard connector for connecting it to the connection capillaries.

Figure 27:
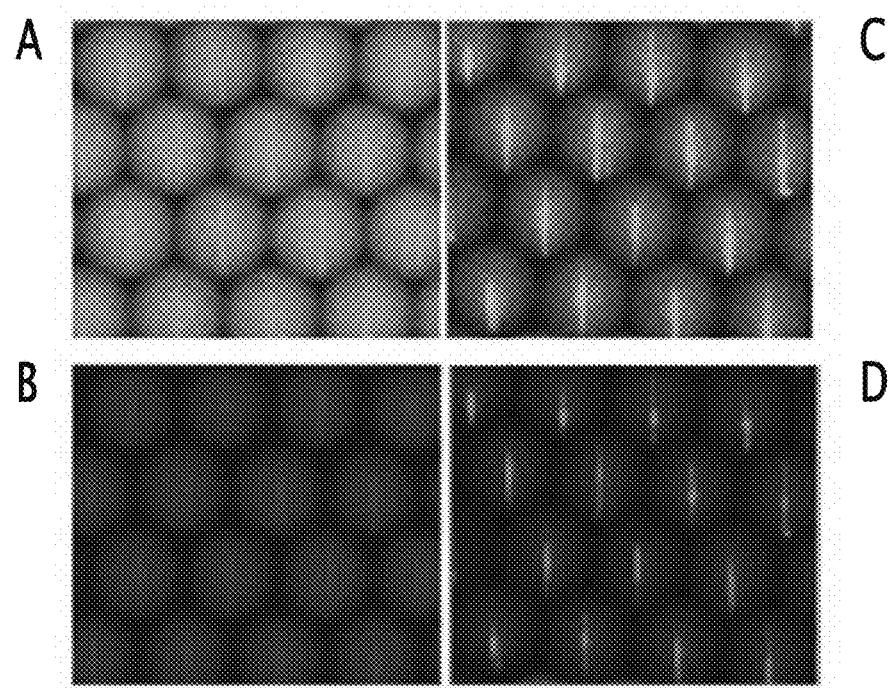

This experiment gives the possibility of showing the possibility of making a binding test on magnetic particles in a column in the drops with two fluorescence readings of secondary reagents as this is illustrated by FIG. 27. In the absence of any monoclonal antibody, a dispersed fluorescence of the signaling entity (FIG. 27 A) and of the quantification entity (FIG. 27 B) is observed. Conversely, in the presence of 50 nM of a monoclonal antibody having a binding activity against the antigen (TT7), a re-localization of fluorescence of the signaling entity (FIG. 27 C) and of the quantification entity (FIG. 27 D) is observed.

Figure 28:
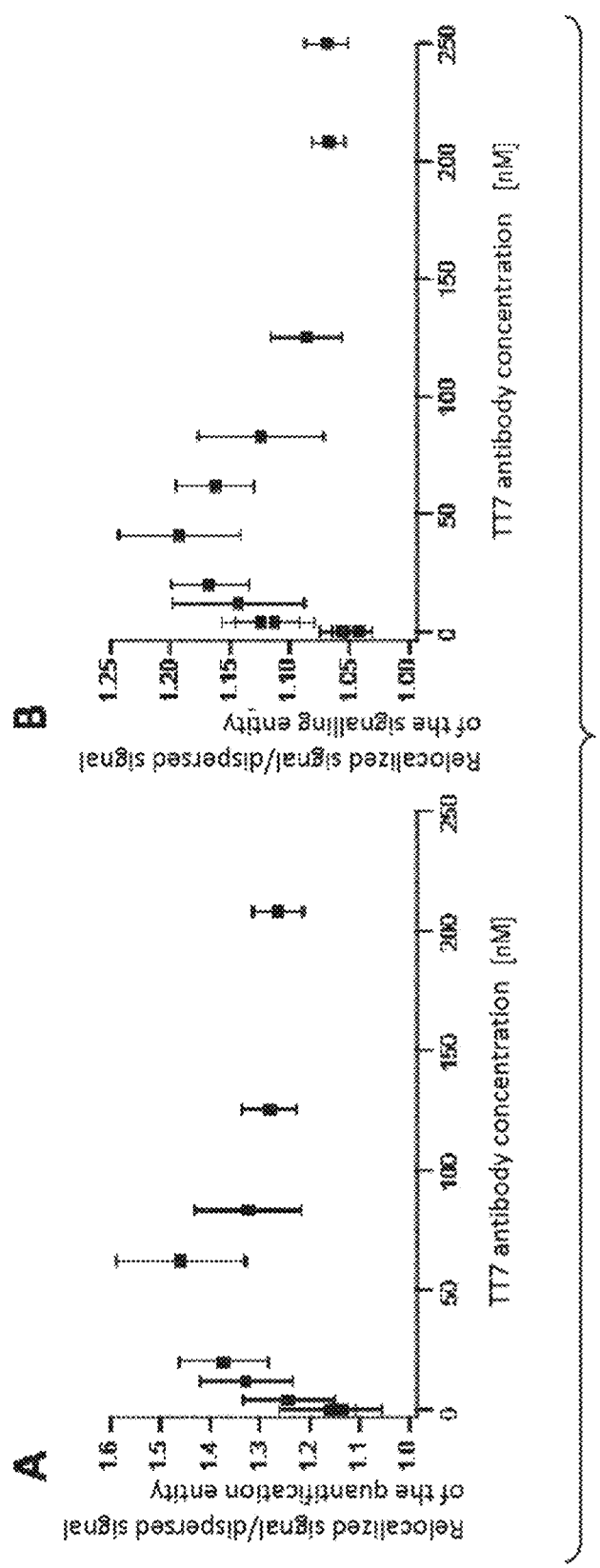

FIG. 28 is a titration curve representing the ratio of the signals re-localized and dispersed of the quantification entities (FIG. 28 A) and of the signaling entities (FIG. 28 B) according to the concentration of a target element (antibody TT7) in nanomolar.

Example 8: Measurement of the Affinity of a Monoclonal Antibody for its ANTIGEN IN A 2D CHAMBER This example is similar in all points to example 7 except that several distinct target elements 37, representing an affinity range for the antigen, are measured.

An object of this example is to demonstrate the possibility of measuring the affinity of a monoclonal antibody for a given antigen in a device of the type 60, i.e. a chamber in which the drops are distributed in two dimensions in a single layer.

The dissociation constant Kd is evaluated from the concentration measurement of florescent antigen bound to the immobilized antibody on the column of beads and from the simultaneous measurement of the concentration of captured antibodies on the bead column.

The antibodies anti-TT used for this experiment, a so called TT4, TT7 and TT10, were obtained by expression of recombinant proteins from sequences published in the article written by Brandon J DeKosky et al., entitled "High-throughput sequencing of the paired human immunoglobulin heavy and light chain repertoire" published in Nature Biotechnology Volume: 31, pages 166 to 169 in 2013.

Different concentrations of each of the three antibodies were used in several distinct emulsions in order to obtain by linear regression the ratio of the signaling entity signal over the signal of the quantification entity respectively for each of the three antibodies, more specifically 0 nM, 5 nM and 10 nM for the antibody TT10, 0 nM, 2.5 nM and 10 nM for the TT4 antibody and 0 nM, 5 nM, 10 nM, 15 nM and 25 nM for the TT7 antibody.

Figure 29:
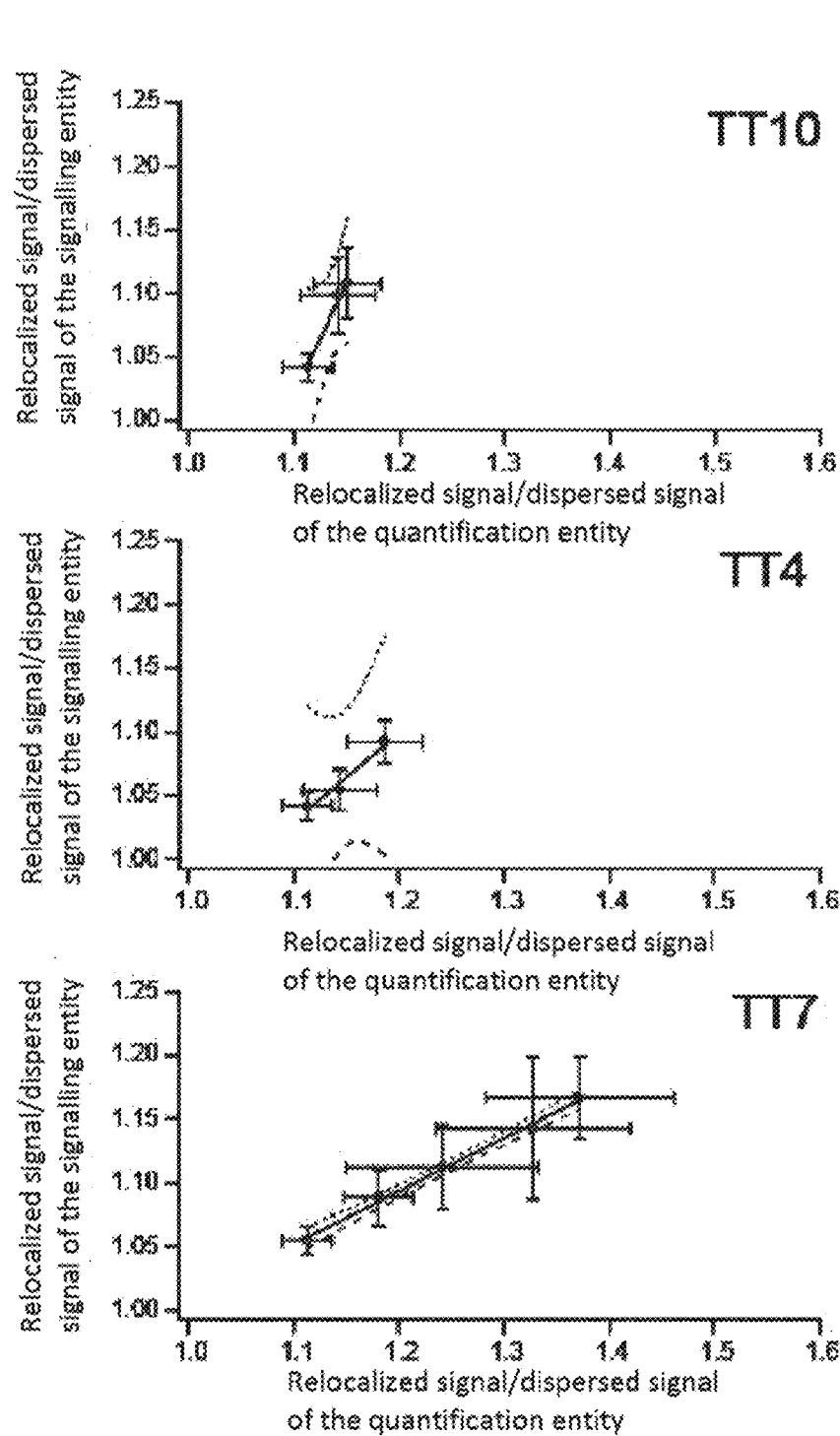
FIGS. 29 and 30 illustrate example 8.
Figure 30:
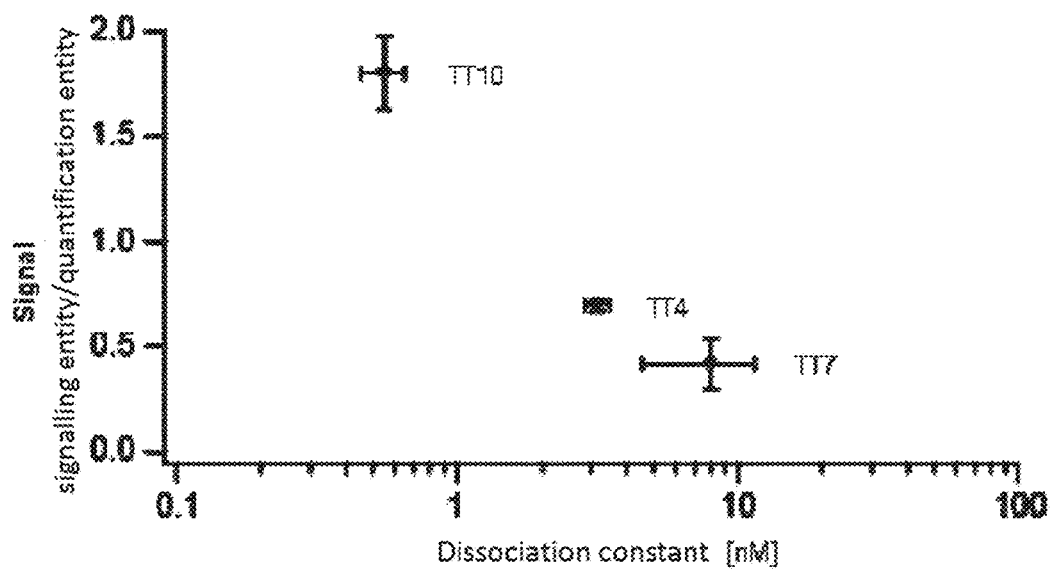

This experiment gives the possibility of showing the possibility of correlating the ratio of the signaling entity signal over the signal of the quantification entity with the dissociation constant of the target element selected as this is illustrated by FIGS. 29 and 30.

FIG. 29 is a graph representing the ratio of the re-localized and dispersed signals of the quantification entities in abscissas and of the signaling entities in ordinates for the three monoclonal antibodies, TT4, TT7 and TT10 tested in this experiment.

FIG. 30 is a graph representing in abscissas the dissociation constant of the three monoclonal antibodies obtained by surface plasmon resonance (SPR) and in ordinates their ratio of the signaling entity signal over the quantification entity signal.

Example 9: Kinetic and Quantitative Measurement of the Secretion of A Monoclonal Antibody by Primary Cells in a 2D Chamber This example is similar in all points with example 8 except that the target element 37 is a monoclonal antibody secreted by a primary cell and that this secretion is measured kinetically.

An object of this example is to demonstrate the possibility of simultaneously measuring the secretion kinetics and the affinity, for a given antigen, of monoclonal antibodies generated by single primary cells isolated in drops in a device of type 60.

As for example 6, the lymphocytes B were extracted beforehand from the spleen of a mouse and purified according to a standard procedure (Pan B kit II #130-104-443, Miltenyi Biotec).

Figure 31:
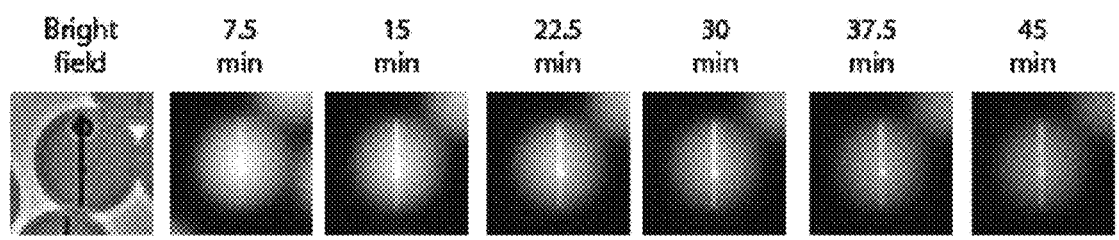
FIGS. 31 and 32 illustrate example 9.
Figure 31:
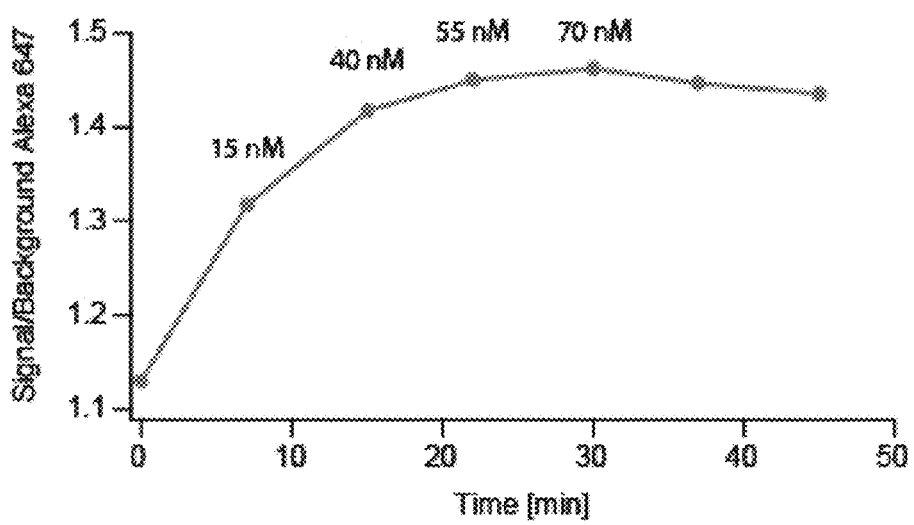

FIG. 31 is a graph representing the time-dependent change, at the scale of the single cell, of the ratio of the re-localized signal of the line of magnetic beads over the dispersed signal of the drop versus time (min). Further, by the titration curve (FIG. 28a of example 7), it is possible to correlate the measured signal with a monoclonal antibody concentration. This concentration is noted in FIG. 30.

Figure 32:
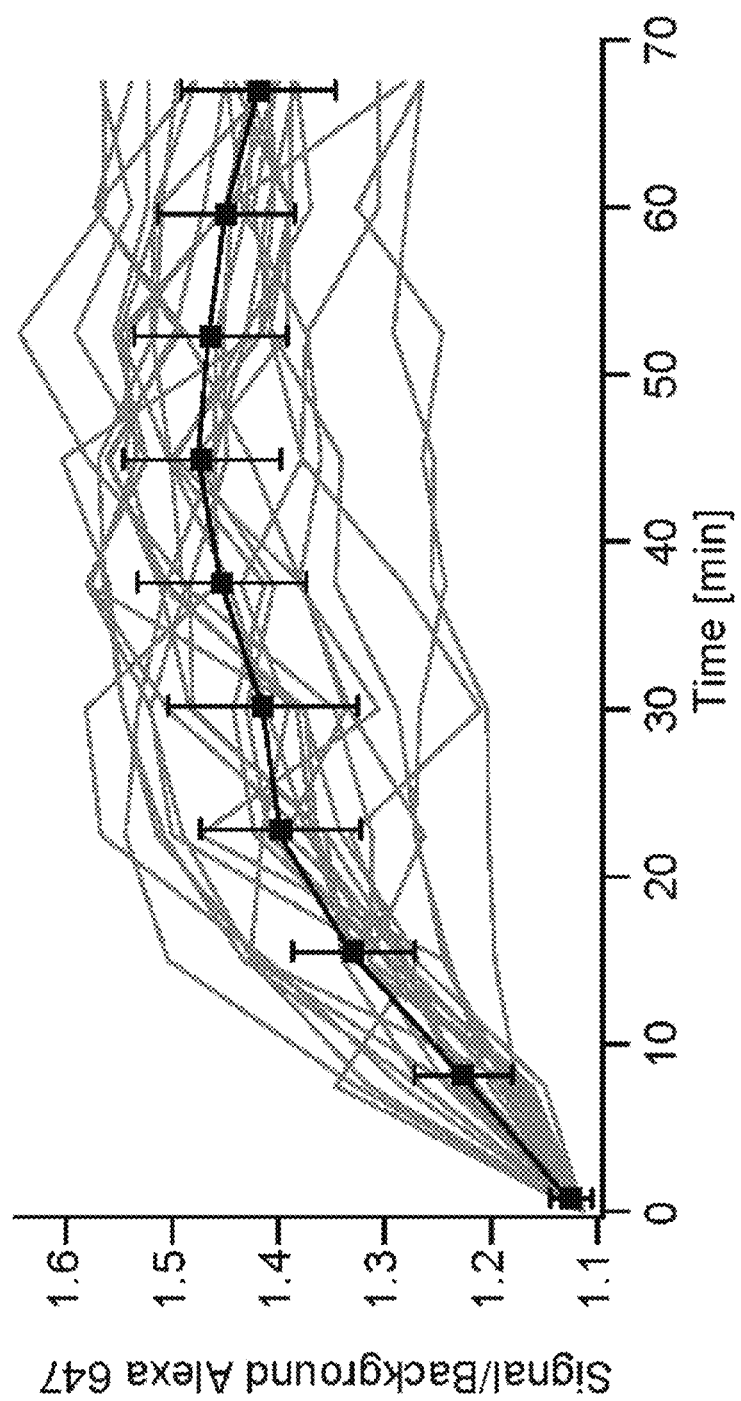

FIG. 32 is a graph representing the time-dependent change, at the scale of the single cell, of the ratio of the re-localized signal of the line of magnetic beads over the dispersed signal of the drop versus time (min) for n=25 distinct primary cells. FIG. 32 illustrates the heterogeneity of the primary cells.

Example 10: Number, Geometry and Stability of the Aggregates of Magnetic Beads in a Drop In this example, the target element 37 is a biotinylated fluorescent molecule, for example AF546-Biotin (Thermo-Fisher #S11225) which also has the role of a signaling entity and which is already contained in the solution to be screened. This example does not apply any cells.

An object of this example is to demonstrate the possibility of stabilizing lines of aggregates of magnetic beads and of ensuring their singularities in the drop, by the use of a transverse binding molecule. In the case of this experiment, we show the use of different concentrations of a multiply biotinylated protein, Biotin-BSA (Sigma Aldrich #A8549) as a transverse binding molecule. The Biotin-BSA used has between 8 and 16 moles of Biotin per mole of Albumin.

In this experiment, the drops measure 40 picoliters.
In this example, the working solution comprises:
50-v-v Serum Super low IgG (#SH30898.03, Thermo Thermo Scientific),
25 mM of HEPES buffer at pH 7.4,
0.1% v/v Pluronic F-68 provided by Life Technologies,
1% v-v Antibiotic-Antimycotic (#15240, ThermoFisher).
The volume of the working solution is completed with DMEM-F12 provided by Life Technologies in order to attain the final volume.

The seven emulsions produced for this experiment, contain the following reagents suspended in the working solution:
a final 100 nM concentration of AF546-Biotin (signaling entity)
once, twice or thrice the standard amount of 33.33% v/v of magnetic particles Streptavidin (Ademtech #0433),
50, 100, 200, 400, 800 or 1,600 nM of Dy-649 (Dyomics),
A variable ratio of Biotin-BSA, magnetic bead, from 0 for 1, 5 or 1.25 for 1 or 100 for 1, i.e. a concentration of Biotin-BSA of 0, 0.5, 2.5, 5 or 15 nM.

A reference emulsion, so called "VHH lines" is produced as described in example "C". In the case of the emulsion "VHH lines", the stabilization of the magnetic bead lines is obtained by the transverse bonding between the target elements (antibodies) and the capture entities ("CaptureSelect™ Biotin Anti-LC-kappa (murine) conjugate" Thermo Fisher #7103152500), because a same target element (antibody) may be bound to two capture entities.

Figure 33:
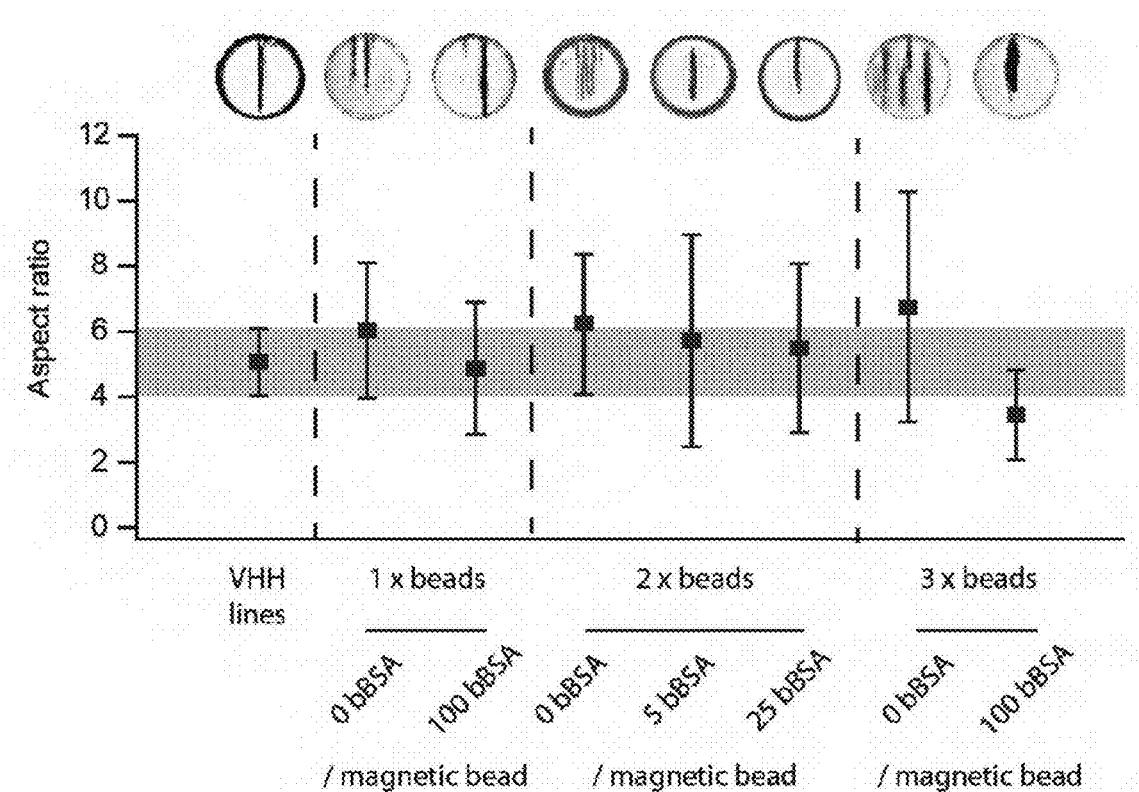
FIGS. 33 and 34 illustrate example 10.

FIG. 33 is a graph representing the format ratio of the line of magnetic beads according to different experimental conditions and illustrated in each case by a microscopic image.

Figure 34:
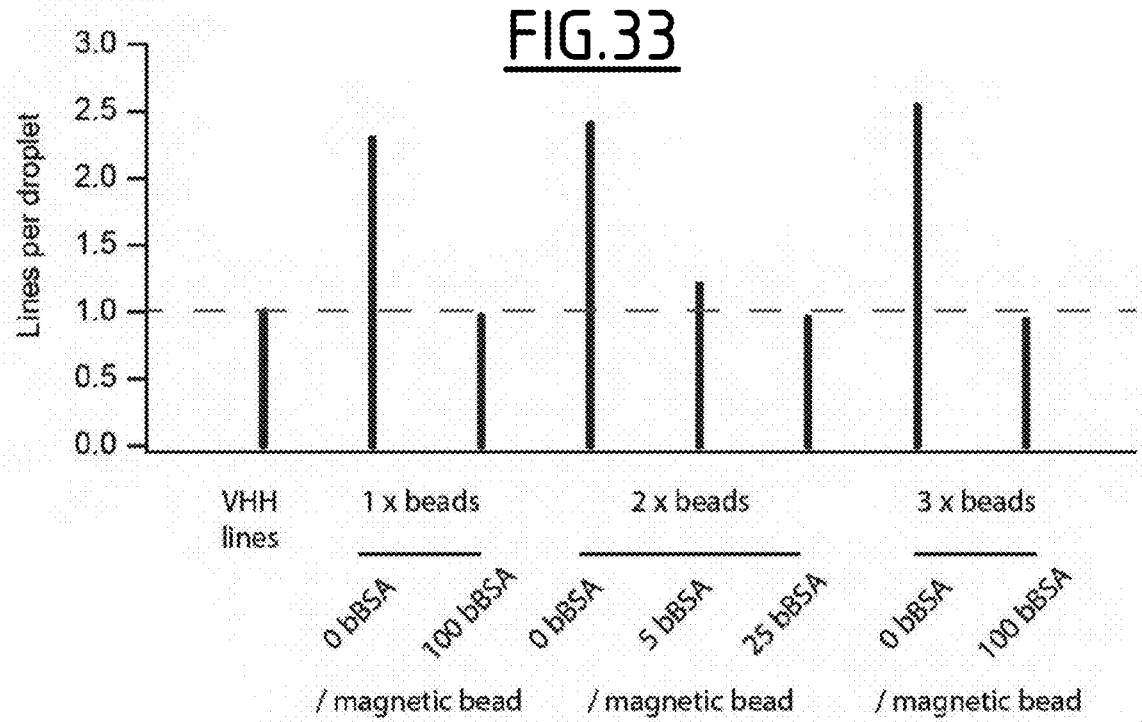

FIG. 34 is a graph representing the singularity or plurality of the line of magnetic beads according to different experimental conditions.

This experiment gives the possibility of showing the possibility of stabilizing the number and the geometry of the lines of magnetic beads per drop as this is illustrated by FIGS. 33 and 34.

The invention claimed is:

1. A method for analyzing the content of drops, comprising the following step:
providing a plurality of drops contained in a carrier fluid, at least one of the drops comprising at least an aggregate of particles defining an elongated object along a main axis, at least certain drops containing at least one target element able to bind to the aggregate,
wherein the aggregate of particles comprises a column oriented along the main axis and the method comprises measuring a physical parameter characteristic of the attachment of the target element on the aggregate, the measuring including measurement of a physical parameter locally in a plurality of points located in the drop, and including the determination of the integral of the measured values within the drop.

2. The method according to claim 1, wherein the particles are superparamagnetic particles.

3. The method according to claim 1 wherein providing the drops comprises:
the dispersion of the particles in a fluid mass intended to form the drops, and then
the dispersion of the fluid mass in the form of drops,
the formation in each drop of at least one aggregate of particles defining an elongated object along a main axis, the aggregate of particles being formed in each drop after the dispersion.

4. The method according to claim 1, wherein the target element is an element selected from the group formed by a protein, an antibody, a peptide, a piece of DNA or RNA, a metabolite, an ion, a lipid and a biomolecule which may be produced by a cell.

5. The method according to claim 1, wherein at least certain drops comprise a productive entity which may produce the target element, the productive entity being selected from the group consisting of a cell and an in vitro expression system.

6. The method according to claim 1, comprising before measuring, orienting the main axis of the aggregate along a detection axis.

7. The method according to claim 1, comprising multiple measurings, with orienting the main axis of the aggregate along a different detection axis for each of the measurings.

8. The method according to claim 1, wherein the measurement step is carried out in a microfluidic chamber without circulation of the drops.

9. The method according to claim 1, comprising:
providing a device comprising an assembly for putting in circulation the drop and a detection area,
the transport of the drop towards the detection area, the measurement within the drop being carried out in the detection area.

10. The method according to claim 1, comprising:
a provision of a device comprising an assembly for putting in circulation the drop and a plurality of classification areas said device capable of directing the drop or a portion of the drop selectively towards a classification area, a decision for classifying the drop or a portion of the drop, the decision comprising selectively selecting a classification area from among the plurality of classification areas, and a transport of the drop respectively of a portion of the drop, towards the classification area of the drop selected during the decision.

11. The method according to claim 1, wherein at least one drop comprises at least one target element, at least one first signaling entity capable of forming a complex with the target element and at least a distinct second signaling entity capable of forming a complex with the target element, the method comprising the measurement of a signal indicating the concentration of each of the signaling entities re-localized on the aggregate.

12. The method according to claim 1, wherein at least one drop comprises at least one target element, at least one signaling entity capable of forming a complex with the target element and at least one quantification entity capable of forming a complex with the target element, the method comprising:

the measurement of a signal representative of the concentration of the signaling entity re-localized on the aggregate, the measurement of a signal representative of the concentration of the quantification entity re-localized on the aggregate, the determination of the dissociation constant of the target element with the signaling entity from the ratio of the signaling entity signal re-localized over the signal of the re-localized quantification entity.

13. The method according to claim 12, wherein at least certain drops comprise a productive entity, the productive entity being a cell which may produce at least one antibody being a target element, the method comprising determining the affinity of the antibody produced by the productive entity for at least one antigen, and sorting out the drop after the determination step.

14. The method according to claim 1, wherein at least one drop comprises at least two distinct signaling entities, each of both signaling entities being capable of forming a complex with a distinct target element on the aggregate, the method comprising the measurement of a signal indicating the concentration of each of the re-localized signaling entities.

15. The method according to claim 14, wherein at least certain drops comprise a productive entity, the productive entity being a cell which may produce one or several types of proteins, each protein being a distinct target element, the measurement of the signal indicating the concentration of each of the re-localized signaling entities allowing quantification of the type(s) of proteins.

16. An apparatus for analyzing the content of drops comprising:

an assembly for providing a plurality of drops contained in a carrier fluid, at least one of the drops comprising at least one aggregate of particles defining an elongated object along a main axis, wherein the aggregate of particles comprises a column oriented along the main axis and the apparatus comprises an assembly for measuring a physical parameter characteristic of the binding of a target element on the aggregate, the assembly for measuring being adapted to measure the physical parameter locally in a plurality of points located in the drop, the measurement step preferably including the determination of the integral of the measured values within the drop, the apparatus further comprising:

an assembly for circulating the drop, an assembly for deciding classification of the drop, and an assembly for sorting out the drop according to the classification decision.

17. The method according to claim 1, wherein the aggregate is generated by permanent magnets.

* * * * *